United States Patent
Snider et al.

(10) Patent No.: US 10,203,339 B2
(45) Date of Patent: Feb. 12, 2019

(54) DIAGNOSIS OF CARDIOVASCULAR DISEASE

(75) Inventors: James V. Snider, Pleasanton, CA (US); Sven Jacobson, New York, NY (US)

(73) Assignee: Critical Care Diagnostics, Inc., San Diego, CA (US)

( * ) Notice: Subject to any disclaimer, the term of this patent is extended or adjusted under 35 U.S.C. 154(b) by 1534 days.

(21) Appl. No.: 12/299,177

(22) PCT Filed: May 1, 2007

(86) PCT No.: PCT/US2007/067914
§ 371 (c)(1),
(2), (4) Date: Sep. 2, 2009

(87) PCT Pub. No.: WO2007/130962
PCT Pub. Date: Nov. 15, 2007

(65) Prior Publication Data
US 2010/0009356 A1    Jan. 14, 2010

Related U.S. Application Data

(60) Provisional application No. 60/796,912, filed on May 1, 2006.

(51) Int. Cl.
*G01N 33/53*    (2006.01)
*G01N 33/68*    (2006.01)

(52) U.S. Cl.
CPC ..... *G01N 33/6869* (2013.01); *G01N 33/6893* (2013.01); *G01N 2333/7155* (2013.01); *G01N 2800/226* (2013.01); *G01N 2800/32* (2013.01); *G01N 2800/325* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Zuk et al. | |
| 5,206,140 A | 4/1993 | Marder et al. | |
| 5,217,899 A | 6/1993 | Shapiro et al. | |
| 5,348,879 A | 9/1994 | Shapiro et al. | |
| 5,786,163 A | 7/1998 | Hall | |
| 6,040,147 A | 3/2000 | Ridker et al. | |
| 6,210,976 B1 | 4/2001 | Sabbadini et al. | |
| 6,288,218 B1 | 9/2001 | Levinson | |
| 6,323,334 B1 | 11/2001 | Kingsbury et al. | |
| 6,677,124 B2 | 1/2004 | Tsuji et al. | |
| 6,810,284 B1 | 10/2004 | Bradley | |
| 6,905,827 B2 | 6/2005 | Wohlgemuth et al. | |
| 7,087,396 B2 | 8/2006 | Tominaga et al. | |
| 7,432,060 B2 | 10/2008 | Lee | |
| 7,655,415 B2 | 2/2010 | Lee | |
| 7,670,000 B2 | 3/2010 | Perie | |
| 7,670,769 B2 | 3/2010 | Lee | |
| 7,985,558 B2 | 7/2011 | Lee | |
| 7,989,210 B2 | 8/2011 | Lee | |
| 7,998,683 B2 | 8/2011 | Snider et al. | |
| 8,090,562 B2 | 1/2012 | Snider et al. | |
| 8,147,817 B2 | 4/2012 | Lee et al. | |
| 8,420,785 B2 | 4/2013 | Snider | |
| 8,530,173 B2 | 9/2013 | Lee | |
| 8,597,958 B2 | 12/2013 | Lee | |
| 8,617,825 B2 | 12/2013 | Snider et al. | |
| 8,728,742 B2 | 5/2014 | Snider | |
| 8,734,769 B2 | 5/2014 | Lee | |
| 8,748,110 B2 | 6/2014 | Snider et al. | |
| 8,748,116 B2 | 6/2014 | Lee | |
| 8,871,452 B2 | 10/2014 | Lee | |
| 9,057,733 B2 | 6/2015 | Snider et al. | |
| 9,150,654 B2 | 10/2015 | Snider | |
| 9,239,333 B2 | 1/2016 | Snider | |
| 9,523,696 B2 | 12/2016 | Snider | |
| 9,551,708 B2 | 1/2017 | Snider et al. | |
| 9,568,481 B2 | 2/2017 | Snider et al. | |
| 9,857,379 B2 | 1/2018 | Lee | |
| 9,934,249 B2 | 4/2018 | Tripathi et al. | |
| 2002/0025559 A1 | 2/2002 | Tsuji et al. | |
| 2002/0072674 A1 | 6/2002 | Criton et al. | |
| 2002/0115081 A1 | 8/2002 | Lee et al. | |
| 2002/0172978 A1* | 11/2002 | Delmas et al. | 435/7.1 |
| 2003/0109420 A1* | 6/2003 | Valkirs et al. | 514/2 |
| 2003/0124624 A1 | 7/2003 | Tominaga et al. | |
| 2003/0228570 A1 | 12/2003 | Yat et al. | |
| 2004/0048286 A1* | 3/2004 | Lee | C12Q 1/6883 435/6.16 |
| 2004/0121343 A1 | 6/2004 | Buechler et al. | |
| 2004/0132013 A1 | 7/2004 | De Bold | |
| 2004/0133079 A1 | 7/2004 | Mazar et al. | |
| 2004/0253637 A1 | 12/2004 | Buechler et al. | |
| 2005/0130136 A1 | 6/2005 | Lee | |
| 2005/0196817 A1 | 9/2005 | Kingsmore et al. | |
| 2005/0203046 A1 | 9/2005 | Schmitz et al. | |
| 2005/0250156 A1 | 11/2005 | Shebuski et al. | |
| 2005/0272054 A1 | 12/2005 | Cargill et al. | |
| 2006/0216755 A1 | 9/2006 | Lee | |
| 2007/0042978 A1 | 2/2007 | Girard et al. | |
| 2007/0248981 A1 | 10/2007 | Snider et al. | |
| 2008/0003199 A1 | 1/2008 | Lee | |
| 2009/0111708 A1 | 4/2009 | Seddon et al. | |
| 2009/0192078 A1 | 7/2009 | Lee | |
| 2009/0264779 A1 | 10/2009 | Snider et al. | |
| 2009/0305265 A1 | 12/2009 | Snider et al. | |
| 2010/0009356 A1 | 1/2010 | Sinder et al. | |
| 2010/0055683 A1 | 3/2010 | Snider et al. | |
| 2010/0267062 A1 | 10/2010 | Frey et al. | |

(Continued)

FOREIGN PATENT DOCUMENTS

| | | |
|---|---|---|
| EP | 1731910 | 12/2006 |
| JP | H05-184384 | 7/1993 |

(Continued)

OTHER PUBLICATIONS

WebMD (Mar. 7, 2007, webmd.com).*

(Continued)

*Primary Examiner* — Michael Szperka
(74) *Attorney, Agent, or Firm* — Fish & Richardson P.C.

(57) ABSTRACT

This invention relates to methods for the detection of cardiovascular disease, e.g., acute coronary syndrome, heart failure and/or pulmonary embolism, in high body mass index (BMI) individuals, e.g., with a BMI of 25-29, or 30 or above, and those with impaired renal function.

18 Claims, 4 Drawing Sheets

(56) References Cited

U.S. PATENT DOCUMENTS

| | | | |
|---|---|---|---|
| 2011/0053170 | A1 | 3/2011 | Snider et al. |
| 2011/0137131 | A1 | 6/2011 | Adourian et al. |
| 2011/0250703 | A1 | 10/2011 | Lee |
| 2011/0256635 | A1 | 10/2011 | Snider |
| 2011/0262941 | A1 | 10/2011 | Snider |
| 2011/0280887 | A1 | 11/2011 | Lee |
| 2012/0040381 | A1 | 2/2012 | Snider et al. |
| 2012/0065897 | A1 | 3/2012 | Snider et al. |
| 2012/0276551 | A1 | 11/2012 | Snider |
| 2013/0071404 | A1 | 3/2013 | Snider et al. |
| 2013/0177931 | A1 | 7/2013 | Snider et al. |
| 2013/0244236 | A1 | 9/2013 | Snider et al. |
| 2013/0251664 | A1 | 9/2013 | Lee |
| 2013/0273562 | A1 | 10/2013 | Lee |
| 2013/0317030 | A1 | 11/2013 | Lee |
| 2013/0345805 | A1 | 12/2013 | Snider et al. |
| 2014/0045200 | A1 | 2/2014 | Snider et al. |
| 2014/0051773 | A1 | 2/2014 | Snider |
| 2014/0058743 | A1 | 2/2014 | Snider et al. |
| 2014/0234875 | A1 | 8/2014 | Snider |
| 2014/0286944 | A1 | 9/2014 | Snider et al. |
| 2014/0302536 | A1 | 10/2014 | Lee |
| 2015/0081224 | A1 | 3/2015 | Snider et al. |
| 2015/0153360 | A1 | 6/2015 | Lee |
| 2015/0177259 | A1 | 6/2015 | Lee |
| 2015/0199491 | A1 | 7/2015 | Snider et al. |
| 2015/0361177 | A1 | 12/2015 | Snider |
| 2016/0169879 | A1 | 6/2016 | Snider et al. |
| 2016/0169882 | A1 | 6/2016 | Snider et al. |
| 2016/0299153 | A1 | 10/2016 | Snider |
| 2018/0156818 | A1 | 6/2018 | Lee |

FOREIGN PATENT DOCUMENTS

| | | |
|---|---|---|
| JP | H06-178687 | 6/1994 |
| JP | 7031479 | 2/1995 |
| JP | 2005-291899 | 10/2005 |
| JP | 2005-538700 | 12/2005 |
| JP | 2007-515632 | 6/2007 |
| JP | 2007-248395 | 9/2007 |
| JP | 2011-520098 | 7/2011 |
| JP | 2012-508386 | 4/2012 |
| RU | 2312591 | 12/2007 |
| RU | 2452394 | 6/2012 |
| WO | WO 98/07754 | 2/1998 |
| WO | WO 98/38311 | 9/1998 |
| WO | WO 98/43090 | 10/1998 |
| WO | WO 99/13331 | 3/1999 |
| WO | WO 99/013331 | 3/1999 |
| WO | WO 99/34217 | 7/1999 |
| WO | 00/35951 | 6/2000 |
| WO | WO 00/35473 | 6/2000 |
| WO | WO 00/73498 | 12/2000 |
| WO | WO 01/021641 | 3/2001 |
| WO | WO 01/070817 | 9/2001 |
| WO | WO 01/70817 | 9/2001 |
| WO | 02/38794 | 5/2002 |
| WO | 03/094856 | 11/2003 |
| WO | WO 03/100000 | 12/2003 |
| WO | WO 04/056868 | 7/2004 |
| WO | 05/041893 | 5/2005 |
| WO | WO 2005/041893 A2 * | 5/2005 |
| WO | WO 05/55810 | 6/2005 |
| WO | WO 05/079844 | 9/2005 |
| WO | WO 06/77265 | 7/2006 |
| WO | WO 07/127749 | 11/2007 |
| WO | WO 07/130627 | 11/2007 |
| WO | WO 07/130962 | 11/2007 |
| WO | WO 07/131031 | 11/2007 |
| WO | WO 07/143295 | 12/2007 |
| WO | WO 09/007754 | 1/2009 |
| WO | WO 09/129454 | 10/2009 |
| WO | WO 11/127412 | 11/2011 |

OTHER PUBLICATIONS

Yale Journal of Medicine and Law, vol. VII, Issue 3, 2011, 8 pages.*
Homeopathic remedies and treatments.com (Nov. 15, 2013, 3 pages, homeopathicremediesandtreatment.com).*
Kenchaiah et al., N Engl J Med, 347 (2002), pp. 305-313.*
The Merck Manual of Diagnosis and Therapy, 17$^{th}$ edition, 1999, Merck Research Laboratories, pp. 1682-1692.*
Weinberg et al., Circulation. Feb. 11, 2003;107(5):721-6.*
Shimpo et al., Circulation. May 11, 2004;109(18):2186-90. Epub Apr. 26, 2004.*
Maxwell et al., Eur J Heart Fail. Mar. 2002;4(2):125-30.*
Anwaruddin et al., "Renal function, congestive heart failure, and amino-terminal pro-brain natriuretic peptide measurement: results from the ProBNP Investigation of Dyspnea in the Emergency Department (PRIDE) Study," J. Am. Coll. Cardiol., 47(1):91-97 (2006).
Baekkevold et al., "Molecular characterization of NF-HEV, a nuclear factor preferentially expressed in human high endothelial venules," Am. J. Path., 163(1):69-79 (2003).
Bayés-Genís Antoni, "The circulating NTproBNP level, a new biomarker for the diagnosis of heart failure in patients with acute shortness of breath," Revista Española de Cardiologia, 58(10):1142-1144 (2005).
Blum et al., "Pathophysiological role of cytokines in congestive heart failure," Annu. Rev. Med., 52:15-27 (2001) (abstract).
Brint et al., "ST2 is an inhibitor of interleukin 1 receptor and Toll-like receptor 4 signaling and maintains endotoxin tolerance," Nat. Immunol., 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med., 30(7):1468-1473 (2004).
Carter et al., "Regulation of ST2L expression of T helper (Th) type 2 cells," Eur. J. Immunol., 31(10):2979-2985 (2001). (Abstract Only).
Figal et al., « [Usefulness of NTproBNP in the emergency management of patients with severe syspnea and an uncertain heart failure diagnosis], Revista Española de Cardiologia, 58(10):1155-1161 (2005).
Fonarow and Heywood, "The confounding issue of comorbid renal insufficiency," Am. J. Med., 119(12A):S17-S25 (2006).
Januzzi et al., "Natriuretic peptide testing for the evaluation of critically ill patients with shock in the intensive care unit: a prospective cohort study," Crit. Care, 10(1):R37 (2006).
Januzzi et al., "NT-proBNP testing for diagnosis and short-term prognosis in acute destabilized heart failure: an international pooled analysis of 1256 patients: the International Collaborative of NT-proBNP Study," Eur. Heart J., 27(3):330-337 (2006).
Januzzi et al., "The N-terminal Pro-BNP investigation of dyspnea in the emergency department (PRIDE) study," Am. J. Cardiol., 95(8):948-954 (2005).
Januzzi et al., "Utility of amino-terminal pro-brain natriuretic Peptide testing for prediction of 1-year mortality in patients with dyspnea treated in the emergency department," Arch. Intern. Med., 166(3):315-320 (2006).
Kida et al., "Pathophysiological role of natriuretic peptides," Rinsho Byori, 37(8):875-882 (1989) Abstract Only.
Knudsen et al., "Predictors of elevated B-type natriuretic peptide concentrations in dyspneic patients without heart failure: an analysis from the breathing not properly multinational study," Ann. Emerg. Med., 45(6):573-580 (2005).
Krauser et al., "Effect of body mass index on natriuretic peptide levels in patients with acute congestive heart failure: a ProBNP Investigation of Dyspnea in the Emergency Department (PRIDE) substudy," Am. Heart J., 149(4):744-750 (2005).
Kumar et al., Expression of ST2, an interleukin-1 receptor homologue, is induced by proinflammatory stimuli. Biochem Biophys Res Commun. Jun. 27, 1997;235(3):474-8.
Kuroiwa et al., "Construction of ELISA system to quantify human ST2 protein in sera of patients. Hybridoma," 19(2):151-159 (2000).

(56) References Cited

OTHER PUBLICATIONS

Lee et al., "Novel markers for heart failure diagnosis and prognosis," Curr Opin Cardiol, 20(3):201-210 (2005).
Leyva et al., "Uric acid in chronic heart failure: a marker of chronic inflammation," European Heart J., 19:1814-1822 (1998).
Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A., 95(12):6930-6935 (1998).
Maisel et al., "Bedside B-Type Natriuretic Peptide in the Emergency Diagnosis of Heart Failure With Reduced or Preserved Ejection Fraction," J. Am. Coll. Cardiol., 41:2010—(2003), 2017.
Maisel et al., "Primary results of the Rapid Emergency Department Heart Failure Outpatient Trial (REDHOT). A multicenter study of B-type natriuretic peptide levels, emergency department decision making, and outcomes in patients presenting with shortness of breath," J. Am. Coll. Cardiol., 44(6):1328-1333 (2004).
McCord et al., "Relationship between obesity and B-type natriuretic peptide levels," Arch. Intern. Med., 164(20):2247-2252 (2004).
Mehra et al., "Obesity and suppressed B-type natriuretic peptide levels in heart failure," J. Am. Coll. Cardiol., 43(9) :1590-1595 (2004)J. Am. Coll. Cardiol., 43(9) :1590-1595 (2004).
Mitcham et al., T1/ST2 signaling establishes it as a member of an expanding interleukin-1 receptor family. J Biol Chem. Mar. 8, 1996;271(10):5777-83.
Mueller et al., "Use of B-type natriuretic peptide in the evaluation and management of acute dyspnea," New England Journal of Medicine, 350(7):647-654 (2004).
Orús et al., Prognostic Value of Serum Cytokines in Patients with Congestive Heart Failure, J Heart Lung Transplant 2000; 19:419-25.
Perrier et al., "D-dimer testing for suspected pulmonary embolism in outpatients," Am. J. Respir. Crit. Care Med., 156(2):492-496 (1997).
Ridker et al., "Inflammation, Aspirin, and the Risk of Cardiovascular Disease in Apparently Healthy Men," New England J. Med., 336:973-979 (1997).
Rohde et al., "Circulating Cell Adhesion Molecules Are Correlated With Ultrasound-Based Assessment of Carotid Atherosclerosis," Arterial Sclerotic Vasc. Biol., 18:1765-1770 (1998).
Rohde et al., "Plasma Concentrations of Interleukin-6 and Abdominal Aortic Diameter Among Subjects Without Aortic Dilatation," Arterial Sclerotic Vasc. Biol., 19:1695-1699 (1999).
Schmitz et al., "IL-33, an interleukin-1-like cytokine that signals via the IL-1 receptor-related protein ST2 and induces T helper type 2-associated cytokines," Immunity, 23(5):479-490 (2005).
Shimpo et al., "Serum levels of the interleukin-1 receptor family member ST2 predict mortality and clinical outcome in acute myocardial infarction" Circulation, 109(18):2186-2190 (2004).
Svensson et al., "Prognostic value of biochemical markers, 12-lead ECG and patient characteristics amongst patients c a l l i ng for an ambulance due to a suspected acute coronary syndrome," Journal of Internal Medicine, 255(4):469-477 (2004).
Tominaga et al., "Nucleotide sequence of a complementary DNA for human ST2," Biochim. Biophys. Acta., 1171:215-218 (1992). (Abstract Only).
Tominaga, FEBS Lett., "A putative protein of a growth specific cDNA from BALB/c-3T3 cells is highly similar to the extracellular portion of mouse interleukin 1 receptor," FEBS Lett., 258:301-304 (1989).
Townsend et al., T1/ST2-deficient mice demonstrate the importance of T1/ST2 in developing primary T helper cell type 2 responses. J Exp Med. Mar. 20, 2000;191(6):1069-76.
Tsutamoto et al., Interleukin-6 spillover in the peripheral circulation increases with the severity of heart failure, and the high plasma level of interleukin-6 is an important prognostic predictor in patients with congestive heart failure. J Am Coll Cardiol. Feb. 1998;31(2):391-8.
Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.

Vidal et al., Prognostic Value of Cytokines and Neurohormones in Severe Heart Failure, Rev Esp Cardiol 2002; 55(5):481-6.
Wang et al., "Expression of Interleukin-1β, Interleukin-1 Receptor, and Interleukin-1 Receptor Antagonist mRNA in Rat Carotid Artery after Balloon Angioplasty," Biochem. Biophyl. Res. Comm., 271:138-143 (2000).
Weinberg et al., "Expression and regulation of ST2, an interleukin-1 receptor family member, in cardiomyocytes and myocardial infarction," Circulation, 106(23):2961-2966 (2002).
Weinberg et al., "Identification of serum soluble ST2 receptor as a novel heart failure biomarker," Circulation, 107(5):721-726 (2003).
Yamaoka et al., Anti-inflammatory cytokine profile in human heart failure: behavior of interleukin-10 in association with tumor necrosis factor-alpha. Jpn Circ J. Dec. 1999;63(12):951-6.
Yanagisawa et al., The expression of ST2 gene in helper T cells and the binding of ST2 protein to myeloma-derived RPMI8226 cells. J Biochem (Tokyo). Jan. 1997;121(1):95-103.
Zebrack et al., Usefulness of high-sensitivity C-reactive protein in predicting long-term risk of death or acute myocardial infarction in patients with unstable or stable angina pectoris or acute myocardial infarction. Am J Cardiol. Jan. 2002.
U.S. Appl. No. 13/782,326, filed Mar. 1, 2013, Snider.
U.S. Appl. No. 13/787,137, filed Mar. 6, 2013, Snider.
U.S. Appl. No. 13/788,276, filed Mar. 7, 2013, Lee.
U.S. Appl. No. 13/788,922, filed Mar. 7, 2013, Lee.
U.S. Appl. No. 13/787,975, filed Mar. 7, 2013, Snider.
U.S. Appl. No. 13/789,941, filed Mar. 8, 2013, Lee.
U.S. Appl. No. 13/897,249, filed May 17, 2013, Snider.
Examination Report dated Aug. 17, 2012 in corresponding Australian Patent Application No. 2011203031.
Examination Report dated Jan. 29, 2010 in corresponding Australian Patent Application No. 2007248160.
Examination Report dated Oct. 26, 2011 in corresponding Canadian Patent Application No. 2,650,963.
Examination Report dated Aug. 18, 2010 in corresponding Canadian Patent Application No. 2,650,963.
European Search Report dated Sep. 30, 2009 in corresponding European Patent Application No. 07761666.2.
European Search Report dated Jul. 4, 2012 in corresponding European Patent Application No. 12152464.9.
English-language translation of Japanese Office Action dated Oct. 27, 2001 in corresponding Japanese Patent Application No. 2009-510021.
English-language translation of Japanese Office Action dated Oct. 22, 2012 in corresponding Japanese Patent Application No. 2009-510021.
International Preliminary Report on Patentability dated May 1, 2006 in corresponding International Patent Application No. PCT/US07/67914.
International Search Report dated Jul. 22, 2008 in corresponding International Patent Application No. PCT/US07/67914.
Mayo, DD., et al., "Brain natriuretic peptide (BNP) testing in the emergency department," *J. Emerg. Med.* Aug. 2006; 31 (2):201-10 (Abstract only).
U.S. Appl. No. 15/410,155, filed Jan. 19, 2017, Snider et al.
U.S. Appl. No. 15/409,283, filed Jan. 18, 2017, Snider et al.
U.S. Appl. No. 15/370,049, filed Dec. 6, 2016, Snider et al.
U.S. Appl. No. 15/382,810, filed Dec. 19, 2016, Snider.
U.S. Appl. No. 15/385,095, filed Dec. 20, 2016, Snider et al.
U.S. Appl. No. 29/503,093, filed Sep. 23, 2014, Snider et al.
U.S. Appl. No. 29/503,097, filed Sep. 23, 2014, Snider et al.
U.S. Appl. No. 29/503,095, filed Sep. 23, 2014, Snider et al.
Communication in European Patent Application No. 12152464.9, dated Dec. 18, 2013, 5 pages.
Examiner's Report in Canadian Patent Application No. 2,650,963 dated Aug. 17, 2015, 5 pages.
Extended European Search Report and Search Opinion for European Patent Application No. 15198075.2, dated Jul. 20, 2016, 9 pages.
Notice of Reasons for Rejection in Japanese Patent Appl. No. 2009-510021 dated Oct. 27, 2011, 3 pages (English translation).
Notice of Reasons for Rejection in Japanese Patent Appl. No. 2009-510021 dated Oct. 22, 2012, 2 pages (English translation).

(56) References Cited

OTHER PUBLICATIONS

Notice of Reasons for Rejection in Japanese Patent Appl. No. 2014-261824, dated Nov. 30, 2015, 2 pages (English translation).
Written Opinion of International Searching Authority for PCT/US2007/067914, dated Jul. 22, 2008 (7 pages).
U.S. Appl. No. 15/410,155, filed Jan. 19, 2017.
U.S. Appl. No. 15/409,283, filed Jan. 18, 2017.
U.S. Appl. No. 15/370,049, filed Dec. 6, 2016.
U.S. Appl. No. 15/382,810, filed Dec. 19, 2016.
U.S. Appl. No. 15/385,095, filed Dec, 20, 2016.
U.S. Appl. No. 29/503,093, filed Sep. 23, 2014.
U.S. Appl. No. 29/503,097, filed Sep. 23, 2014.
U.S. Appl. No. 29/503,095, filed Sep. 23, 2014.
'www.accessdata.fda.gov' [online]. "Substantial Equivalence Determination Decision Summary Assay Only Template," Dec. 26, 2011 [retrieved on Nov. 28, 2017]. Retrieved from the Internet: URL < https:// https://www.accessdata.fda.gov/cdrh_docs/reviews/k111452.pdf>, 17 pages.
Allen and Felker, "Multi-marker strategies in heart failure: clinical and statistical approaches," Heart Fail. Rev., 15: 343-349 (2010).
Alleyne et al., "Cytochrome-c as Marker for MI 97 Cytochrome-c Detection a Diagnostic Marker for Myocardial Infarction," Applied Biochemistry and Biotechnology, 90: 97-105 (2001).
Auer et al., "C-reactive protein and coronary artery disease," Jpn. Heart J., 43(6):607-619 (2002).
Aukrust et al., "Cytokine network in congestive heart failure secondary to ischemic or idiopathic dilated cardiomyopathy," Am J Cardiol., 83(3):376-382 (1999).
Australian Office Action in Application No. 2016201172, dated Mar. 28, 2017, 8 pages.
Baggish et al., "A validated clinical and biochemical score for the diagnosis of acute heart failure: The ProBNP Investigation of Dyspnea in the Emergency Department (PRIDE) Acute Heart Failure Score," Am. Heart J. 151:48-54 (2006).
Baumgarten et al., "Cytokines as emerging targets in the treatment of heart failure," Trends Cardiovasc Med., 10(5):216-223 (2000).
Belch et al., "Oxygen free radicals and congestive heart failure," Br. Heart J., 65(5):245-248 (1991).
Boisot et al., "Serial Sampling of ST2 Predicts 90-Day Mortality Following Destabilized Heart Failure," Journal of Cardiac Failure, 14:732-738 (2008).
Brown, "Techniques for Mechanical Stimulation of cells in vitro: a review," Journal of Biomechanics, 33:3-14 (2000).
Canadian Office Action in Application No. 2,650,963, dated Nov. 1, 2017, 18 pages.
Canadian Office Action in Application No. 2,720,674, dated Oct. 30, 2017, 9 pages.
Canadian Office Action issued in Canadian Application No. 265201, dated Jun. 5, 2017, 12 pages.
Canadian Office Action issued in Canadian Application No. 2720674, dated Jan. 19, 2016, 15 pages.
Chan et al., "Human IL018 Receptor and ST2L are Stable and Selective Markers for the Respective Type I and Type 2 Circulating Lymphocytes," J. Immunol. 167(3) 1238-1244 (2001) (abstract).
Cheng et al., Mechanical strain tightly controls fibroblast growth factor-2 release from cultured human vascular smooth muscle cells. Circ Res. 80(1):28-36 (1997). (Abstract).
Chinese Office Action in Application No. 201380054795.8, dated Jul. 6, 2017, 9 pages (with English translation).
Conklin, "B-type Natriuretic Peptide: A New Measurement to Distinguish Cardiac From Pulmonary Causes of Acute Dyspnea," Journal of Emergency Nursing, 31(1):73-75 (2005).
Coyle et al., "Crucial role of the interleukin 1 receptor family member T1/ST2 in T helper cell type 2-mediated lung mucosal immune responses," J. Exp. Med., 190(7):895-902 (1999).
Dale et al., Interleukin-1 Receptor Cluster: Gene Organization of IL1R2, IL1R1, IL1RL2 (IL-1Rrp2), IL1RL1 (T1/ST2), and IL18R1 (IL-1Rrp) on Human Chromosome 2q,) Genomics, 57:177-179 (1999).

De Keulenaer et al., "Identification of IEX-1 as a biomechanically controlled nuclear factor-kappaB target gene that inhibits cardiomyocyte hypertrophy," Circ Res., 90(6):690-696 (2002).
Dhalla et al., "Measurement of adrenolutin as an oxidation product of catecholamines in plasma," Mol. Cell. Biochem., 87:85-92 (1989).
Di Serio et al., "Integration between point-of-care cardiac markers in an emergency/cardiology department and the central laboratory: methodological and preliminary clinical evaluation," Clin. Chem. Lab. Med., 43: 202-209 (2005).
en.wikipedia.org [online]. "ST2 cardiac biomarker," dated Jul. 14, 2012 [retrieved on Feb. 29, 2016]. Retrieved from the Internet: <https://en.wikipedia.org/w/index.php?title=ST2_cardiac_biomarker&oldid=502 1 98259>. 3 pages.
European Extended Search Report for Application No. 15198075.2, dated Jul. 20, 2016, 11 pages.
European Office Action in Application No. 15198075.2, dated Jun. 1, 2017, 6 pages.
European Office action in European Application No. 14188319, dated Jan. 4, 2016, 5 pages.
European Office Action in European Application No. 15163587.7, dated May 22, 2017, 4 pages.
European Office Action in European Application No. 16158762.1, dated May 17, 2017, 6 pages.
Extended European Search Report in Application No. 14177846.4, dated Jan. 5, 2015, 5 pages.
Extended European Search Report in Application No. 16166093.1, dated Sep. 12, 2016, 7 pages.
Extended European Search Report in Application No. 17177530.7, dated Aug. 28, 2017, 11 pages.
Extended European Search Report in European Application No. 15163587.7, dated Feb. 11, 2016, 8 pages.
McCullough et al., "B-type natriuretic peptide and renal function in the diagnosis of heart failure: an analysis from the Breathing Not Properly Multinational Study," Am. J. Kidney Dis., 41(3):571-579 (2003).
Moe et al., "Neurohormonal activation in severe heart failure: relations to patient death and the effect of treatment with flosequinan," Am. Heart. J., 139:587-95 (2000).
Morgan et al.; "Diagnostic Evaluation of Dyspnea"; American Family Physician 57(4):711-716 (1998); retrieved from http://www.aafp.org/aft/1998/0215/p711.html?printable-afp on Apr. 4, 2012.
Morrison et al., "Utility of a Rapid B-Natriuretic Peptide Assay in Differentiating Congestive Heart Failure from Lung Disease in Patients Presenting With Dyspnea," Journal of American College of Cardiology, 39: 202-209 (2002).
Mueller et al. Use of B-Type Natriuretic Peptide for the Management of Women With Dyspnea, Am J Cardiol 94:1510-1514 (2004).
Mueller et al., "Increased Plasma Concentrations of Soluble ST2 are Predictive for 1-Year Mortality in Patients with Acute Destabilized Heart Failure," Clinical Chemistry, 54:752-756 (2008).
Mukoyama et al., Augmented secretion of brain natriuretic peptide in acute myocardial infarction. Biochem Biophys Res Commun. 180(1):431-6 (1991). (Abstract Only).
Murphy et al., "Signaling and transcription in T helper development," Annu Rev. Immunol. 18:451-94 (2000).
Murray et al., "Chronic beta-adrenergic stimulation induces myocardial proinflammatory cytokine expression," Circulation. 101(20):2338-41 (2000).
Nakano et al., "Characterization of Soluble Thrombomodulin Fragments in Human Urine," Thromb. Haemost. 79(2):331-337 (1998).
Nakano et al., "Elevation of Soluble Thrombomodulin Antigen Levels in the Serum and Urine of Streptozotocin-Induced Diabetes Model Rats," Thrombosis Research 99:83-91 (2000).
Ng et al., "Diagnosis of heart failure using urinary natriuretic peptides," Clin. Sci. (Lond). 106(2):129-33 (2004).
Nichols et al., "The influence of 'diastolic' length on the contractility of isolated cat papillary muscle," J Physiol. 361:269-79 (1985).
Non-Final Office Action in U.S. Appl. No. 13/282,111, dated Feb. 2, 2016, 9 pages.
Non-Final Office Action in U.S. Appl. No. 13/787,137, dated Sep. 12, 2016, 18 pages.

(56) References Cited

OTHER PUBLICATIONS

Non-Final Office Action in U.S. Appl. No. 14/312,221, dated Sep. 20, 2016, 39 pages.
Notice of Reasons for Rejection; Japanese Patent Application No. 2012-100940; dated Jan. 8, 2014, 6 pages (with English translation).
Nozaki et al., "Soluble Tumor Necrosis Factor Receptors are Elevated in Relation to Severity of Congestive Heart Failure," Jpn. Circ. J. 61:657-64 (1997).
O'Neill et al., "The IL-1 receptor/toll-like receptor superfamily: crucial receptors for inflammation and host defense," Immunol. Today. 21(5):206-9 (2000).
Office Action in Australian Application No. 2013305829, dated Mar. 21, 2018, 3 pages.
Office Action in Australian Application No. 2016200419, dated Jan. 12, 2017, 7pages.
Extended European Search report in European Application No. 16158762, dated Jun. 10, 2016, 9 pages.
Feldman et al., "C-reactive protein is an independent predictor of mortality in women with HIV-1 infection," J. Acquir. Immune Defic. Syndr., 32(2):210-214 (2003). (abstract).
Feng et al., "Transcriptional profile of mechanically induced genes in human vascular smooth muscle cells," Circ. Res., 85(12):1118-23 (1999).
Final Office Action issued in U.S. Appl. No. 14/244,526, dated Aug. 30, 2016, 14 pages.
Final Office Action issued in U.S. Appl. No. 14/523,694, dated Nov. 17, 2016, 8 pages.
Forssmann et al., "The heart is the center of a new endocrine, paracrine, and neuroendocrine system," Arch. Histol. Cytol., 52 Suppl:293-315 (1989). (Abstract).
Frangogiannis et al., "Resident cardiac mast cells degranulate and release preformed TNF-alpha, initiating the cytokine cascade in experimental canine myocardial ischemia/reperfusion," Circulation., 98(7):699-710 (1998).
Galvani et al., "Prognostic influence of elevated values of cardiac troponin I in patients with unstable angina," Circulation, 95(8):2053-2059 (1997). (Abstract).
Gegenhuber et al., "B-type natriuretic peptide and amino terminal proBNP predict one-year mortality in short of breath patients independently of the baseline diagnosis of acute destabilized heart failure," Clinica Chimica Acta, 370(1-2):174-179 (2006).
Goetze et al., "B-type natriuretic peptide and its precursor in cardiac venous blood from failing hearts," European Journal of Heart Failure, 7(1):69-74 (2005).
Gutstein et al., "Role of inositol 1,4,5-trisphosphate receptors in regulating apoptotic signaling and heart failure," Heart Vessels. Suppl 12:53-7 (1997).
Gwechenberger et al., "Cardiac myocytes produce interleukin-6 in culture and in viable border zone of reperfused infarctions," Circulation. Feb. 2, 1999;99(4):546-51.
Hall et al., "N-terminal proatrial natriuretic factor. An independent predictor of long-term prognosis after myocardial infarction,"; Circulation, 89(5):1934-42 (1994).
Hanyu et al., "Urinary Thrombomodulin in Patients with Rheumatoid Arthritis: Relationship to Disease Subset.," Clin. Rheumatol. 18:385-9 (1999).
Heeschen et al., "Predictive value of C-reactive protein and troponin T in patients with unstable angina: a comparative analysis. CAPTURE Investigators. Chimeric c7E3 AntiPlatelet Therapy in Unstable angina. Refractory to standard treatment trial," J. Am. Coll. Cardiol. 35(6):1535-42 (2000). (Abstract Only.).
Hirota et al., "Loss of a gp130 cardiac muscle cell survival pathway is a critical event in the onset of heart failure during biomechanical stress," Cell, 97(2):189-98 (Apr. 1999).
International Preliminary Report on Patentability for International Application No. PCT/US2013/056020 dated Feb. 24, 2015, 7 pages.
International Search Report and Written Opinion of the International Searching Authority forPCT/US2013/056020 dated Dec. 12, 2013, 11 pages.

Iwahana et al., "Different promoter usage and multiple transcription initiation sites of the interleukin-1 receptor-related human ST2 gene in UT-7 and TM12 cells," Eur. J. Biochem. 264(2):397-406 (1999).
Izakov et al., "Cooperative effects due to calcium binding by troponin and their consequences for contraction and relaxation of cardiac muscle under various conditions of mechanical loading," Circ. Res. 69(5):1171-84 (1991).
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol., 50:607-613 (2007).
Januzzi et al., "The value of soluble ST2 measurement for the diagnostic and prognostic evaluation of patients with acute dyspnea," Circulation, 114(18):721 (2006) (abstract).
Japanese Office Action in Application No. 2015-528625, dated Jun. 5, 2017, 10 pages (with English translation).
Japanese Office Action in Japanese Application No. 2015-173815, dated Aug. 3, 2016, 9 pages (with English translation).
Japanese Office Action in Japanese Application No. 2016-006007, dated Dec. 8, 2016, 4 pages (with English translation).
Joyce et al., "Two inhibitors of pro-inflammatory cytokine release, interleukin-10 and interleukin-4, have contrasting effects on release of soluble p75 tumor necrosis factor receptor by cultured monocytes," Eur. J. Immunol. 24(11):2699-705 (1994).
Kakkar et al., "The IL-33/ST2 pathway: Therapeutic target and novel biomarker," Nature Reviews Drug Discovery, 7(10):827-840 (2008).
Kieser et al., "Identification of the primary growth response gene, ST2/T1, as a gene whose expression is differentially regulated by different protein kinase C isozymes," FEBSLett., 372(2-3):189-193 (1995).
Kip et al.; "The problem with composite end points in cardiovascular studies," J. Am. Coll. Cardiol. 51:701-707 (2008).
Kumar et al., "ST2/T1 protein functionally binds to two secreted proteins from Balb/c 3T3 and human umbilical vein endothelial cells but does not bind interleukin 1," J. Biol. Chem., 270(46):27905-27913 (1995).
Kurioiwa et al., "Identification of Human ST2 Protein in the Sera of Patients with Autoimmune Diseases," Biochemical and Biophysical Research Communications 284:1104-8 (2001).
Laine et al., "Effect of ryanodine on atrial natriuretic peptide secretion by contracting and quiescent rat atrium," Pflugers Arch., 426(3-4):276-83 (1994).
Lammerding et al., "Mechanotransduction in cardiac myocytes," Ann. N. Y. Acad. Sci., 1015:53-70 (2004).
MacGowan et al., "Circulating interleukin-6 in severe heart failure," Am J Cardiol., 79(8):1128-31 (1997).
MacKenna et al., Role of mechanical factors in modulating cardiac fibroblast function and extracellular matrix synthesis. Cardiovasc. Res., 46(2):257-63 (2000).
Maisel et al., "Rapid measurement of B-type natriuretic peptide in the emergency diagnosis of heart failure," N. Engl. J. Med., 347(3):161-167 (2002).
Mann et al., Stress activated cytokines and the heart., Cytokine Growth Factor Rev. 7(4):341-54 (1996).
Office Action in Canadian Application No. 2,650,201, dated Apr. 26, 2018, 6 pages.
Office Action in Chinese Application No. 201380054795.8, dated Mar. 6, 2018, 8 pages (English translation).
Office Action in European Application No. 13831501.5, dated May 23, 2018, 11 pages.
Office Action in European Application No. 15163587.7, dated Feb. 14, 2018, 4 pages.
Office Action in European Application No. 15198075.2, dated Jan. 17, 2018, 5 pages.
Office Action in Japanese Application No. 2017-162932, dated Jun. 27, 2018, 8 pages (with English Translation).
Office Action in Japanese Application No. 2017-178945, dated Jul. 5, 2018, 8 pages (with English Translation).
Office Action in Russian Application No. 2015110054, dated Jun. 7, 2018, 16 pages (with English translation).
Office Action in U.S. Appl. No. 13/787,137, dated Apr. 6, 2017, 6 pages.

(56) References Cited

OTHER PUBLICATIONS

Office Action in U.S. Appl. No. 14/290,465, dated Jan. 30, 2017, 17 pages.
Office Action in U.S. Appl. No. 14/312,221, dated Jan. 25, 2018, 46 pages.
Oh et al.; Diastolic Heart Failure Can Be Diagnosed by Comprehensive Two-Dimensional and Doppler Echocardiography; Journal of American College of Cardiology; 2006, vol. 47, pp. 500-506.
Ohki et al., "Identification of mechanically induced genes in human monocytic cells by DNA microarrays," J. Hypertens. 20(4):685-691 (2002).
Ohki et al., "Identification of mechanically induced genes in human monocytic cells by DNA microarrays." J. Hypertens., 20(4):685-691 (2002) (Abstract Only).
Ohtsuka et al., "Effect of beta-blockers on circulating levels of inflammatory and anti-inflammatory cytokines in patients with dilated cardiomyopathy," J. Am. Coll. Cardiol. 37(2):412-7 (2001).
Onda et al., "Identification of Genes Differentially Expressed in Canine Vasospastic Cerebral Arteries After Subarachnoid Hemorrhage," Journal of Cerebral Blood Flow & Metabolism 19:1279-1288 (1999).
Ørntoft et al., "Genome-wide study of gene copy numbers, transcripts, and protein levels in pairs of non-invasive and invasive human transitional cell carcinomas," Mol. Cell. Proteomics. 1(1):37-45.
Oshikawa et al., "Acute eosinophilic pneumonia with increased soluble ST2 in serum and bronchoalveolar lavage fluid," Respir. Med., 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Oshikawa et al., "Expression and function of the ST2 gene in a murine model of allergic airway inflammation," Clin. Exp. Allergy, 32(10):1520-1526 (2002).
Oshikawa et al., "Expression of ST2 in helper T lymphocytes of malignant pleural effusions," Am. J. Respir. Crit. Care Med., 165(7):1005-1009 (2002).
Oshikawa et al., "ST2 protein induced by inflammatory stimuli can modulate acute lung inflammation," Biochem. Biophys. Res. Commun., 299(1):18-24 (2002).
Papetropoulos et al., "Nitric oxide synthase inhibitors attenuate transforming-growth-factor-beta 1-stimulated capillary organization in vitro." Am. J. Pathol. 150(5):1835-44 (1997).
Pascual Figal et al., "Usefulness of NTproBNP in the emergency management of patients with severe syspnea and an uncertain heart failure diagnosis," Revista Española de Cardiologia 58(10):1155-1161 (2005).
Potter et al., "Mutations in the murine fitness 1 gene result in defective hematopoiesis." Blood,90(5):1850-7 (1997).
Prabhu et al., "beta-adrenergic blockade in developing heart failure: effects on myocardial inflammatory cytokines, nitric oxide, and remodeling." Circulation. 101(17):2103-9 (2000).
Richards et al., "Plasma N-terminal pro-brain natriuretic peptide and adrenomedullin: new neurohormonal predictors of left ventricular function and prognosis after myocardial infarction," Circulation, 97:1921-1929 (1998).
Ridker et al.,"C-reactive protein and other markers of inflammation in the prediction of cardiovascular disease in women," N. Engl. J. Med., 324: 836-843 (2000).
Roig et al., "Serum interleukin-6 in congestive heart failure secondary to idiopathic dilated cardiomyopathy," Am. J. Cardiol. 82(5):688-90, A8 (1998).
Russian Office Action in Application No. 2015110054, dated Jun. 21, 2017, 15 pages (with English translation).
Sabatine et al., "Complementary Roles for Biomarkers of Biomechanical Strain ST2 and N-Terminal Prohormone B-Type Natriuretic Peptide in Patients With ST-Elevation Myocardial Infarction", Circulation, 117(15): 1936-1944 (2008).
Sabatine et al., "Multimarker approach to risk stratification in non-ST elevation acute coronary syndromes: simultaneous assessment of troponin I, C-reactive protein, and B-type natriuretic peptide," Circulation, 105(15):1760-1763 (2002).
Saccani et al., "Divergent effects of LPS on expression of IL-1 receptor family members in mononuclear phagocytes in vitro and in vivo," Cytokine, 10(10): 773-80 (1998).
Schaffer et al., "Device for the application of a dynamic biaxially uniform and isotropic strain to a flexible cell culture membrane," J. Orthop. Res. 12(5):709-19 (1994).
Selvais et al., "Direct comparison between endothelin-1, N-terminal proatrial natriuretic factor, and brain natriuretic peptide as prognostic markers of survival in congestive heart failure," J. Card. Fail.,6(3):201-7 (2000). (Abstract Only).
Shimizu et al., "Functional SNPs in the distal promoter of the ST2 gene are associated with atopic dermatitis," Hum. Mol. Genet., 14(19):2919-2927 (2005).
Silver et al., "BNP Consensus Panel 2004: A clinical approach for the diagnostic, prognostic, screening, treatment monitoring, and therapeutic roles of natriuretic peptides in cardiovascular diseases," Congest. Heart Fail., 10(5 suppl. 3):1-30 (2004).
Singapore Office Action in Singapore Application No. 11201501271T, 12 pages, dated Aug. 6, 2016.
Strunk et al., "Impact of the history of congestive heart failure on the utility of B-type natriuretic peptide in the emergency diagnosis of heart failure: results from the Breathing Not Properly Multinational Study," Am. J. Med., 119(1):69 e1-11 (2006).
Sussman et al., "Dance band on the Titanic: biomechanical signaling in cardiac hypertrophy," Circ Res. 91(10):888-98 (2002).
Sutton et al., "Left ventricular remodeling after myocardial infarction: pathophysiology and therapy," Circulation. 101(25):2981-8 (2000).
Tajima et al., "The increase in serum soluble ST2 protein upon acute exacerbation of idiopathic pulmonary fibrosis," Chest, 124(4):1206-1214 (2003).
Tang et al. "Gene Expression profiling during the transition to failure in TNF-α over-expressing mice demonstrates the development of autoimmune myocarditis," Journal of Molecular and Cellular Cardiology36:515-30 (2004).
Tominaga et al., [ST2 gene: a gene that is induced by growth stimulation and encoding a product highly similar to the interleukin 1 receptors] Seikagaku. 67(5):356-64 (1995). Review. Japanese with translation.
Tominaga et al., "The existence of a growth-specific DNA binding factor for the promoter region of mouse ST2 gene," FEBS Lett. 354(3):311-4 (1994).
Trehu et al., "Phase I trial of interleukin 2 in combination with the soluble tumor necrosis factor receptor p75 IgG chimera," Clin. Cancer Res. 2(8):1341-51 (1996).
Tsuchiya et al., "Th1, Th2 and activated T-cell marker and clinical prognosis in peripheral T-cell lymphoma unspecified comparison AILD, ALCL, lymphoblastic lymphoma and ATLL," Blood, 103:236-241 (2004).
Tung et al., "Amino-Terminal Pro-Brain Natriuretic Peptide for the Diagnosis of Acute Heart Failure in Patients with Previous Obstructive Airway Disease," Annals of Emergency Medicine, 48(1):66-74 (2006).
Tung et al., "Influence of stretch on excitation threshold of single frog ventricular cells," Exp. Physiol. 80(2):221-35 (1995).
Tung et al., "Utility of B-type natriuretic peptide for the evaluation of intensive care unit shock," Crit. Care Med., 32(8):1643-1647 (2004).
Vahl et al., "Length dependence of calcium- and force-transients in normal and failing human myocardium," J. Mol. Cell. Cardiol. 30(5):957-66 (1998).
Yamamoto et al., "Regulation of cardiomyocyte mechanotransduction by the cardiac cycle," Circulation., 103(10):1459-64 (2001).
Yamamoto et al., "Induction of tenascin-C in cardiac myocytes by mechanical deformation. Role of reactive oxygen species," J. Biol. Chem. 274(31):21840-6 (1999).
Yamamoto et al., "Mechanical strain suppresses inducible nitric-oxide synthase in cardiac myocytes," J. Biol. Chem. 273(19):11862-6 (1998).

(56) References Cited

OTHER PUBLICATIONS

Yanagisawa et al., "Murine ST2 gene is a member of the primary response gene family induced by growth factors," FEBS Lett., 302(1):51-53 (1992).

Yanagisawa et al., "Presence of a novel primary response gene ST2L, encoding a product highly similar to the interleukin 1 receptor type 1," FEBS Lett. 318(1):83-87 (1993).

Yanagisawa et al., "The expression of ST2 gene in helper T cells and the binding of ST2 protein to myeloma-derived RPMI8226 cells," J. Biochem. (Tokyo). 121(1):95-103 (1997).

Yasue et al., "Localization and Mechanism of Secretion of B-Type Natriuretic Peptide in Comparison with Those of A-Type Natriuretic Peptide in Normal Subjects and Patients with Heart Failure," Circulation 90:195-203 (1994).

* cited by examiner

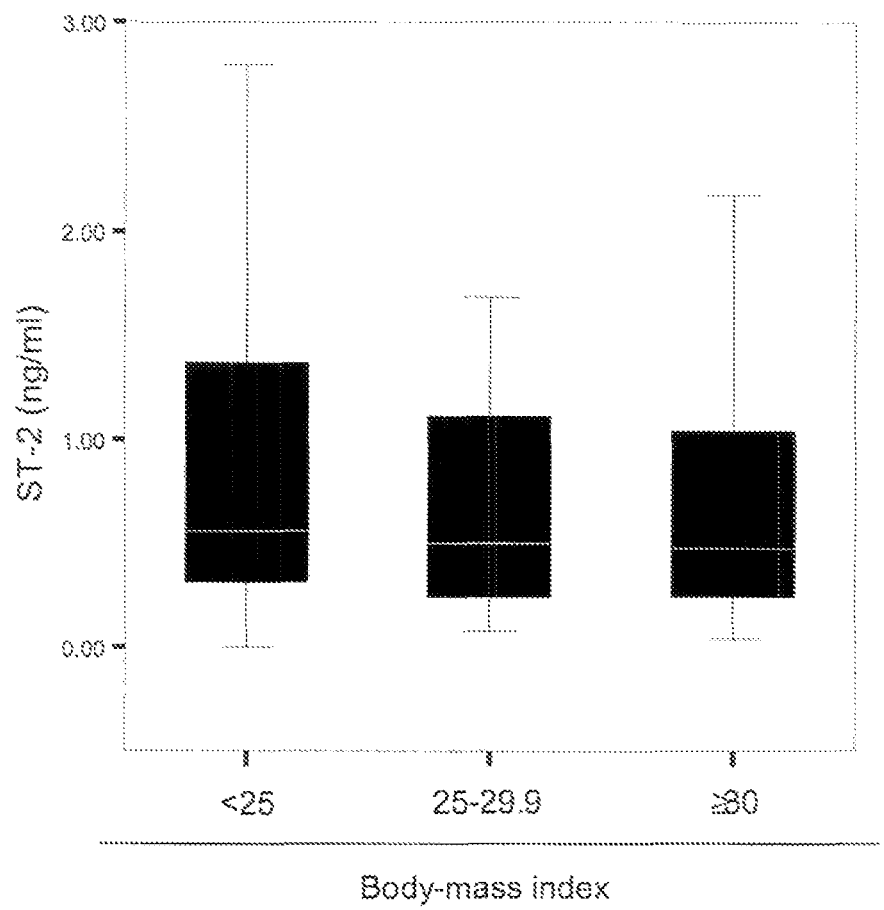
Figure 4
FIGURE 5A
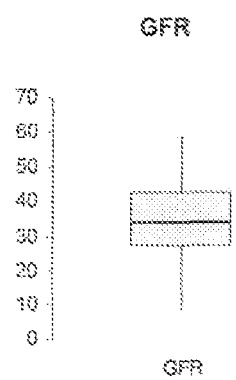
FIGURE 5B
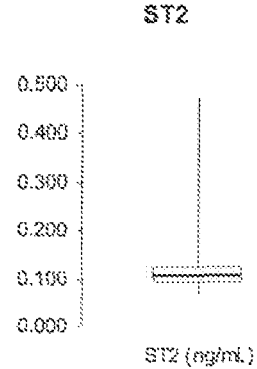

DIAGNOSIS OF CARDIOVASCULAR DISEASE

CROSS-REFERENCE TO RELATED APPLICATIONS

This application is the U.S. national stage under 35 USC § 371 of International Application Number PCT/US2007/067914, filed on May 1, 2007, which claims the benefit under 35 USC § 119(e) to U.S. Provisional Patent Application Ser. No. 60/796,912, filed on May 1, 2006, the entire contents of which are hereby incorporated by reference.

TECHNICAL FIELD

This invention relates to methods for the detection of heart failure and pulmonary embolism in high body mass index (BMI) individuals and those with impaired renal function.

BACKGROUND

Levels of natriuretic peptides such as B-type natriuretic peptide (BNP) and N terminal-pro BNP (NT-proBNP) have been shown to be diagnostic of cardiovascular disease (Clerico and Emdin, Clin. Chem. 50:33-50 (2004)). However, it is known and accepted in the field that certain subjects have levels of natriuretic peptide that are lower than expected relative to a "normal" subject for the same level of disease. The exact mechanism for this phenomenon is not known. These subjects include people with impaired renal function (Anwaruddin et al., J. Am. Coll. Cardiol. 47(1): 91-7 (2006); McCullough et al., Am. J. Kidney Dis. 41(3): 571-9 (2003)), and those who are overweight (Body Mass Index (BMI) of 25-29) or obese (BMI≥30) (Krauser et al., Am. Heart J. 149(4):744-50 (2005); McCord et al., Arch. Intern. Med. 164(20):2247-52 (2004)).

SUMMARY

The present invention is based, at least in part, on the surprising discovery that, unlike the natriuretic peptides (NPs), the biomarker ST2 (also known as Interleukin 1 Receptor Like-1 (IL1RL1)) is not affected by high body mass index (BMI) or by impaired renal function, and therefore provides better prognostic and diagnostic information than NPs in subjects with high (BMI) or impaired renal function. Thus, the methods described herein include determining whether a subject has a high BMI and/or has renal failure, and if the subject has one or both conditions, selecting the subject, and determining levels of IL1LR1, and, optionally, BNP and/or D-dimer in the subject. These methods can be used to diagnose cardiovascular disease (CVD), e.g., acute coronary syndrome (ACS), heart failure (HF), and pulmonary embolism (PE) in the subject, e.g., in subjects with dyspnea.

In some embodiments, the methods include determining levels of IL-33 in addition to or as an alternative to determining levels of ST2.

In one aspect, the invention provides methods for diagnosing cardiovascular disease (CVD), e.g., acute coronary syndrome (ACS), heart failure (HF), or pulmonary embolism (PE) in a subject who has a body mass index (BMI) of greater than or equal to 25. The methods include determining the subject's BMI, and if the subject's BMI is equal to or greater than 25, selecting the subject; and determining levels of ST2, and optionally one or both of BNP level and D-dimer level, in the subject's blood, plasma, or serum. The relationship of the ST2 level to a reference level of ST2, e.g., a reference level that represents a level of ST2 in a subject who does not have CVD, indicates whether the subject has CVD. In some embodiments, if the subject's BNP level is less than 500 pg/mL, e.g., 100-500 pg/mL, and the D-dimer level is less than 500 µg/L, then the relationship of the ST2 level to a reference level of ST2, e.g., a reference level that represents a level of ST2 in a subject who does not have HF, indicates whether the subject has HF. In some embodiments, if the subject's BNP level is less than 100 pg/mL, and the D-dimer level is 500-4000 µg/L, then the relationship of the ST2 level to a reference level of ST2, e.g., a reference level that represents a level of ST2 in a subject who does not have PE, indicates whether the subject has PE.

In another aspect, the invention provides methods for diagnosing cardiovascular disease (CVD), e.g., acute coronary syndrome (ACS), heart failure (HF), or pulmonary embolism (PE) in a subject who has impaired renal function. The methods include evaluating the subject's renal function, and if the subject has impaired renal function, selecting the subject; and determining an ST2 level, and optionally BNP level and/or D-dimer level, in the subject's blood, plasma or serum. The relationship of the ST2 level to a reference level of ST2, e.g., a reference level that represents a level of ST2 in a subject who does not have CVD, indicates whether the subject has CVD. In some embodiments, if the subject's BNP level is less than 500 pg/mL, e.g., 100-500 pg/mL, and the D-dimer level is less than 500 µg/L, then the relationship of the ST2 level to a reference level of ST2, e.g., a reference level that represents a level of ST2 in a subject who does not have HF, indicates whether the subject has HF. In some embodiments, if the subject's BNP level is less than 100 pg/mL, and the D-dimer level is 500-4000 µg/L, then the relationship of the ST2 level to a reference level of ST2, e.g., a reference level that represents a level of ST2 in a subject who does not have PE, indicates whether the subject has PE.

In some embodiments, the reference level represents a level in a subject who does not have CVD, e.g., does not have ACS, HF, and/or PE. In some embodiments, e.g., wherein the biomarker level of ST2 is measured using an immunoassay, e.g., an enzyme-linked immunosorbent assay (ELISA), e.g., as described in Example 1, the reference level is about 0.2 to 0.3 ng/ml, e.g., the level can be 0.20, 0.23, 0.25, 0.27, or 0.29 ng/ml of serum, and values above that level indicate the presence of CVD, e.g., ACS, HF and/or PE. If an analytical technique other than the ELISA described in Example 1 is employed, the reference ST2 level may be different than described herein. However, the specific numbers recited herein should be construed to be equivalent to corresponding numbers generated using other analytical techniques.

In general, determining a level of ST2, BNP, and/or D-dimer in a subject includes obtaining a biological sample from the subject, contacting binding compositions to the sample, wherein the binding compositions specifically bind to ST2, BNP and D-dimer, and measuring or determining the specific binding of the binding composition to the sample. The binding compositions can be, e.g., antibodies that bind specifically to ST2, BNP, and D-dimer polypeptides (e.g., an anti-ST2 Ab, an anti-BNP Ab, and an anti-D-dimer Ab), or oligonucleotide probes that bind specifically to ST2, BNP and D-dimer polynucleotides (e.g., an ST2-specific probe, a BNP-specific probe, and a D-dimer-specific probe).

The methods can also include determining levels of one or more additional biomarkers, e.g., NT-proANP, proANP, ANP, troponin, CRP, creatinine, Blood Urea Nitrogen (BUN), liver function enzymes, albumin, and bacterial endotoxin.

In some embodiments, determining whether a subject has impaired renal function includes determining a glomerular filtration rate (GFR) and/or serum creatinine level. The subject has mildly, moderately, or severely impaired renal function if they have a GFR or serum creatinine level shown in Table 1:

TABLE 1

| Grade | GFR (ml/minute) | Serum Creatinine (μmol/liter) |
| --- | --- | --- |
| mild | 20-50 | 150-300 |
| moderate | 10-20 | 300-700 |
| severe | <10 | >700 |

Also provided herein are kits for diagnosing cardiovascular disease (CVD), that include three different antibodies that specifically bind to ST2, BNP, and D-dimer polypeptides, respectively, or three different nucleic acid probes that specifically bind to nucleic acids encoding ST2, BNP, and D-dimer, respectively, and instructions for use in a method described herein.

"Upregulated," as used herein, refers to increased expression of a gene and/or its encoded polypeptide. "Increased expression" refers to increasing (i.e., to a detectable extent) replication, transcription, and/or translation of IL-33, since upregulation of any of these processes results in an increase in concentration/amount of the polypeptide encoded by the gene. Conversely, "downregulation," or "decreased expression" as used herein, refers to reduced replication, transcription, and/or translation of the IL-33 gene and/or its encoded polypeptide. The upregulation or downregulation of gene expression can be directly determined by detecting an increase or decrease, respectively, in the level of mRNA for the gene, or the level of protein expression of the gene-encoded polypeptide, using any suitable means known to the art, such as nucleic acid hybridization or antibody detection methods, respectively, and in comparison to controls. "Expression," as used herein, refers to nucleic acid and/or polypeptide expression.

As used herein, a "subject" is a mammal, e.g., a human. In all embodiments, human nucleic acids, polypeptides, and human subjects can be used.

As used herein, a "biological sample" includes one or more of blood, serum, plasma, urine, and body tissue. In some embodiments, a sample is a serum or blood sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4 is a box graph of ST2 levels in subjects with various BMIs (<25, 25-29, and ≥30), showing no significant difference in ST2 levels between the BMIs.

FIGS. 5A-B are box graphs illustrating mean Glomerular Filtration Rate (GFR, 5A) and ST2 levels (5B) in a population of 133 subjects with moderate to severe renal insufficiency.

DETAILED DESCRIPTION

Figure 1:
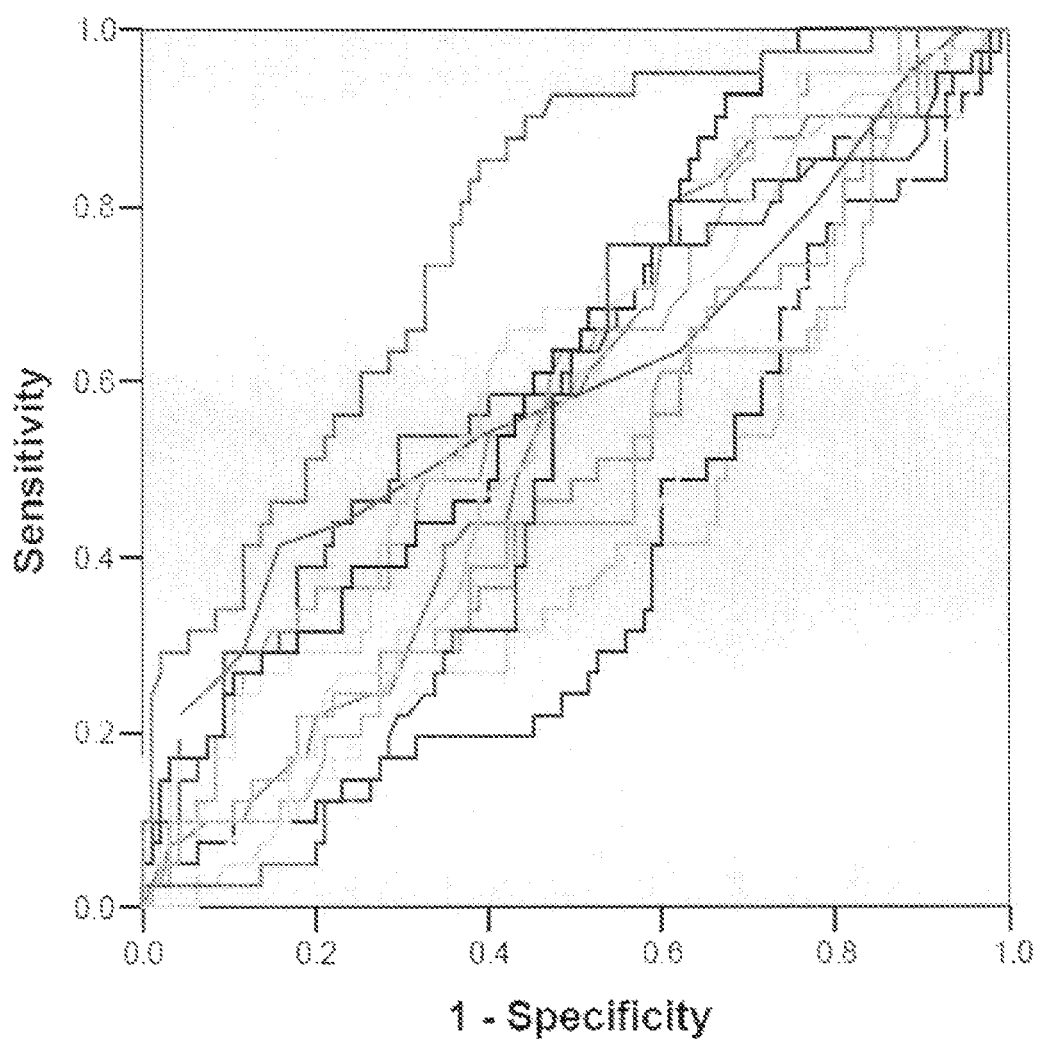
FIG. 1 is a Receiver Operating Characteristics (ROC) curve of the Second Prospective Randomized Amlodipine Survival Evaluation (PRAISE-2) study, illustrating the characteristics of the study population for age, weight, height, BMI, left ventricular ejection fraction (LVEF), creatinine, ST2t1, norepinephrine (NEt1), epinephrine (Et1), dopamine (DAt1), angiotensin (ANGt1), malondialdehyde (MDAt1), adrenolutin (ADRt1), ANPt1, and BNPt1. "t1" refers to a level taken at a first time.

Clinical evaluation of cardiovascular disease (CVD) using natriuretic peptides (NPs) in subjects with high body mass index (BMI) or impaired renal function is complicated by the fact that these subjects have levels of natriuretic peptide that are lower than expected relative to a "normal" subject for the same level of disease. The exact mechanism for this phenomenon is not known. However, one theory, not meant to be limiting, is that lower NP levels in obese and overweight subjects and those with impaired renal function may be related to the clearance mechanisms for NPs, which may have both a renal and epithelial component. ST2, although possibly produced in a similar manner as NPs, does not suffer from these limitations. Therefore, the methods described herein include the use of ST2 (and/or IL-33, the ligand for ST2) in these special subjects, for whom NPs may provide misleading information.

General Methodology

General methods for using levels of ST2 for diagnosis are described in, e.g., U.S. Pat. App. No. 2004/0048286 to Lee et al., the entire contents of which are incorporated herein by reference. The methods described herein are particularly useful in populations of subjects for whom NPs are less useful in the diagnosis and prognosis of CVD. These subjects include those with high BMI, e.g., overweight subjects (BMI of 25-29) or obese subjects (BMI≥30). Thus, in some embodiments, the methods include determining a subject's BMI, and if the subject is overweight or obese, selecting the patient (e.g., selecting the subjects on the basis of their BMI). These subjects also include those with renal impairment. Thus, in some embodiments, the methods include determining whether a subject has impaired renal function, and if the subject has impaired renal function, selecting the patient.

In general, the methods described herein include evaluating levels of ST2 in a biological sample (e.g., a blood, serum, plasma, urine, or body tissue sample), and optionally BNP and/or D-dimer in a subject, e.g., a mammal, e.g., a human. These levels provide information regarding the presence of CVD, e.g., HF and/or PE in a subject. For example, a diagnosis of CVD, e.g., HF in a subject with an ambiguous level of BNP can be confirmed by the presence of elevated ST2 and low D-dimer levels. A diagnosis of CVD, e.g., PE in a subject with ambiguous levels of D-dimer can be confirmed by the presence of high ST2 and low BNP.

Evaluating circulating levels of ST2, BNP, or D-dimer in a subject typically includes obtaining a biological sample, e.g., serum or blood, from the subject. Levels of ST2, BNP, and D-dimer in the sample can be determined by measuring levels of polypeptide in the sample, using methods known in the art and/or described herein, e.g., immunoassays such as enzyme-linked immunosorbent assays (ELISA). Alternatively, levels of ST2, BNP, and D-dimer mRNA can be measured, again using methods known in the art and/or described herein, e.g., by quantitative PCR or Northern blotting analysis.

An antibody that "binds specifically to" an antigen, binds preferentially to the antigen in a sample containing other proteins. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin. The antibody can be polyclonal, monoclonal, recombinant, e.g., a chimeric or humanized, fully human, non-human, e.g., murine, monospecific, or single chain antibody. In some embodiments it has effector function and can fix complement.

A "probe" is a nucleic acid that is at least 10, and less than 200 (typically less than about 100 or 50) base pairs in length. A probe that "binds specifically to" a target nucleic acid hybridizes to the target under high stringency conditions. As used herein, the term "hybridizes under high stringency conditions" describes conditions for hybridization and washing. As used herein, high stringency conditions are 0.5 M sodium phosphate, 7% SDS at 65° C., followed by one or more washes at 0.2 X SSC, 1% SDS at 65° C. Methods for performing nucleic acid hybridization assays are known to those skilled in the art and can be found in Ausubel et al., Eds., *Current Protocols in Molecular Biology*, John Wiley & Sons, N.Y. (1989), 6.3.1-6.3.6.

Detection can be facilitated by coupling (e.g., physically linking) the antibody or probe to a detectable substance (e.g., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, (β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive materials include $^{125}$I, $^{131}$I, $^{35}$S or $^{3}$H.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals, see, e.g., Le Doussal et al., New Engl. J. Med. 146:169-175 (1991); Gibellini et al., J. Immunol. 160:3891-3898 (1998); Hsing and Bishop, New Engl. J. Med. 162:2804-2811 (1999); Everts et al., New Engl. J. Med. 168:883-889 (2002). Various assay formats exist, such as radioimmunoassays (RIA), ELISA, and lab on a chip (U.S. Pat. Nos. 6,176,962 and 6,517,234).

Known techniques in biochemistry and molecular biology can be used in the methods described herein (see, e.g., Maniatis et al., *Molecular Cloning, A Laboratory Manual*, Cold Spring Harbor Laboratory Press, Cold Spring Harbor, N.Y. (1982); Sambrook and Russell, *Molecular Cloning*, 3$^{rd}$ ed., Cold Spring Harbor Laboratory Press, Cold Spring Harbor, N.Y. (2001); Wu, *Recombinant DNA*, Vol. 217, Academic Press, San Diego, Calif. (1993); and Ausbel et al., *Current Protocols in Molecular Biology*, Vols. 1-4, John Wiley and Sons, Inc. New York, N.Y. (2001)).

Once a level of ST2 has been determined, the level can be compared to a reference level, or directly correlated with a value known to correspond to the presence or absence of CVD. In some embodiments, the reference level will represent a threshold level, above which the subject has CVD, e.g., ACS, PE, or HF, and/or has a given severity of CVD, e.g., ACS, HF, or PE, e.g., severe disease. The reference level chosen may depend on the methodology used to measure the levels of ST2. For example, in some embodiments, where circulating levels of soluble ST2 are determined using an immunoassay, e.g., as described herein, the reference level is about 0.2 to 0.3 ng/ml, e.g., 0.20, 0.23, or 0.29 ng/ml of serum, and a level of ST2 above that reference level indicates that the subject has CVD, e.g., ACS, PE, or HF, and/or has severe CVD, e.g., severe ACS, PE, or HF; these reference levels apply when the levels are determined using the method describe in Example 1 herein. In some embodiments, the reference level is a range of levels.

In some embodiments, the methods described herein include determining levels of IL-33 in addition to, or as an alternative to, ST2. In some embodiments, both levels of ST2 and IL-33 are determined, and the information from the comparison of both biomarkers with their respective reference levels provides cumulative information regarding the presence of CVD, and/or presence of severe CVD in the subject. In some embodiments, the ratio of ST2 to IL-33 may be determined, and the ratio compared to a reference ratio that represents a threshold ratio above which the subject has CVD, and/or has severe CVD. Alternatively or in addition, the presence and/or levels of IL-33/ST2 complexes can be determined and compared with a reference level to provide information regarding the presence of CVD, e.g., ACS, PE, or HF, in a subject; for example, levels of the complex above a selected threshold would indicate that the subject has CVD, e.g., ACS, PE, or HF.

In some embodiments, the methods include the use of additional diagnostic methods. Any diagnostic methods known in the art can be used, and one of skill in the art will be able to select diagnostic methods that are appropriate for the subject's symptoms. In some embodiments, the methods described herein include other diagnostic methods in addition to or as an alternative to the measurement of other biomarkers, e.g., physical measurements of lung function or cardiac function as are known in the art.

Thus, the methods described herein can also include measuring levels of ST2, optionally BNP and/or D-dimer, and one or more additional biomarkers, e.g., biomarkers that aid in the subject's diagnosis. As one example, for a subject who has chest pain or dyspnea, biomarkers indicative of cardiac or cardiovascular disease can be measured, e.g., cardiac troponin (cTn), e.g., cTnI or cTnT, NT-proBNP, proBNP, NT-proANP, proANP, and/or ANP; alternatively or in addition, additional biomarkers of pulmonary disease can be measured. Thus, in subjects presenting with symptoms that include MI in their differential diagnoses, the methods can include measuring levels of cTnI, to determine whether the subject is having an MI. One of skill in the art will appreciate that there are a number of additional diagnostic methods that can be used, depending on the situation and the subject's condition.

Also included herein are kits that include a reagent for the detection of ST2, BNP, and D-dimer polypeptide or nucleic acid, e.g., antibodies (i.e., antibodies that bind specifically to one of ST2, BNP, and D-dimer polypeptides), or nucleic acid probes (i.e., probes that are complementary to all or part of one of ST2, BNP, and D-dimer nucleic acids) and instructions for use in a method described herein.

The methods described herein are useful in the diagnosis of subjects with CVD, e.g., ACS, PE, or HF. In the methods described herein, if an overweight or obese subject (e.g., a subject with a BMI of 25-29, or 30 or above) has ambiguous, e.g., low or moderate, BNP (i.e., <500 pg/ml of serum), D-dimer levels of less than 500 µg/L of plasma, and elevated ST2 (e.g., levels above a reference, e.g., 0.2 ng/ml of serum), then the subject can be diagnosed with CVD, e.g., HF and treated accordingly, e.g., with surgical or pharmaceutical intervention, and/or lifestyle change, in spite of the low or moderate BNP levels. Examples of pharmaceutical treatment for heart failure can include angiotensin (renin-angiotensin) system inhibitors such as renin inhibitors, ACE inhibitors, and angiotensin II antagonists, and beta-adrenergic receptor blockers.

In the methods described herein, if a subject (e.g., a subject with a BMI of 25-29, or 30 or above) has low BNP (i.e., <100 pg/ml of serum), ambiguous D-dimer levels, e.g., 500-4000 µg/L of plasma, and elevated ST2 (e.g., levels above a reference, e.g., 0.2 ng/ml of serum), then the subject can be diagnosed with CVD, e.g., PE, and treated accordingly, e.g., with anticoagulant therapy, in spite of their ambiguous D-dimer levels.

ST2/Interleukin 1 Receptor-Like 1 (IL1RL1)

The ST2 gene is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The transmembrane form of ST2 is thought to play a role in modulating responses of T helper type 2 cells (Lohning et al., Proc. Natl. Acad. Sci. U.S.A. 95(12):6930-5 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2 (IL1RL1), which is a soluble secreted form; and ST2L, a transmembrane receptor form that is very similar to the interleukin-1 receptors. The HUGO Nomenclature Committee designated the human homolog of ST2, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID # 601203, and UniGene No. Hs.66. In general, in the methods described herein, the soluble form of ST2 polypeptide is measured.

Methods for detecting and measuring ST2 are known in the art, e.g., as described in U.S. Pat. Pub. Nos. 2003/0124624, 2004/0048286 and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

In some embodiments, the level of ST2 is determined once, e.g., at presentation. In some embodiments, the level of ST2 is determined at one or more of 2, 4, 6, 8, 12, 18, and/or 24 hours, and/or 1-7 days after the onset of symptoms.

In some embodiments, the level of ST2 is determined more than once; in that case, the higher measurement can be used. In embodiments where the level of ST2 is determined more that once, the highest level can be used, or the change in levels can be determined and used. Levels of ST2 can also be determined multiple times to evaluate a subject's response to a treatment. For example, a level of ST2 taken after administration of a treatment, e.g., one or more doses or rounds of a treatment, can be compared to levels of ST2 before the treatment was initiated, e.g., a baseline level. The change in ST2 levels would indicate whether the treatment was effective; e.g., a reduction in ST2 levels would indicate that the treatment was effective.

In some embodiments, the methods include determining the identity of the nucleotide sequence at RefSNP ID: rs1041973.

Interleukin-33 (IL-33)

In the methods described herein, IL-33 can be measured instead of or in addition to ST2.

IL-33 was recently identified as the ligand for ST2, and the presence of increased levels of IL-33 in various inflammatory disorders has been described (see Schmitz et al., Immunity 23(5):479-90 (2005); U.S. Pat. Pub. No. 2005/0203046). The ratio of ST2 to IL-33 can also be determined.

IL-33 protein is expressed as an inactive molecule, pre-IL-33, that is activated after cleavage by Caspase I resulting in the active IL-33 peptide as well as the cleavage peptide product, pro-IL-33. Therefore, the methods described herein can include measuring one, two, or all three of mature IL-33, pre-IL-33, and/or pro-IL-33, all of which are included in the term "IL-33."

The nucleic acid sequence of IL-33 can be found at GenBank Acc. No. NM_033439.2, and the polypeptide sequence is at GenBank Acc. No. NP_254274.1. Additional information is available in the public databases at GeneID: 90865, MIM ID # *608678, and UniGene No. Hs.348390. IL-33 is also known as Chromosome 9 Open Reading Frame 26 (C9ORF26); Nuclear Factor from High Endothelial Venules (NFHEV); and Interleukin 33. See also Baekkevold et al., Am. J. Path. 163: 69-79 (2003).

Methods for measuring levels of IL-33 polypeptide and nucleic acid are known in the art, see, e.g., Schmitz et al., Immunity 23(5):479-90 (2005); U.S. Pat. Pub. No. 2005/0203046.

Body Mass Index (BMI)

Obesity influences the expression of BNP in chronic HF. It is known that there is a significant inverse relationship between body mass index (BMI) and BNP levels.

BMI is determined by weight relative to height, and equals a person's weight in kilograms divided by height in meters squared (BMI=kg/m$^2$). Accepted interpretations are given in Table 2.

TABLE 2

| Category | BMI |
| --- | --- |
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Renal Function

Measures of renal function can include serum creatinine results as well as estimated glomerular filtration rate (GFR) (see, e.g., Levey et al., Ann. Intern. Med. 130(6):461-70 (1999)). Renal impairment is usually divided into three grades, shown in Table 3.

TABLE 3

| Grade | GFR (ml/minute) | Serum Creatinine (µmol/liter) |
| --- | --- | --- |
| mild | 20-50 | 150-300 |
| moderate | 10-20 | 300-700 |
| severe | <10 | >700 |

Thus, the methods described herein can include determining a subject's serum creatinine levels and/or GFR. Alternatively, the methods described herein can include reviewing a subject's medical history to determine their serum creatinine levels and/or GFR.

BNP

B-type natriuretic peptide (BNP) is a marker of heart failure. Levels of BNP can be determined, e.g., in whole blood or serum, using standard methodology. For example, a number of assay kits are commercially available, e.g., the Triage BNP Test (Biosite, Inc., San Diego, Calif.), a point-of-care assay that whole blood or plasma and produces results in about 15 minutes; a chemiluminescent sandwich immunoassay (Bayer HealthCare Diagnostics, Tarrytown, N.Y.) for BNP that is run on the ADVIA Centaur and ACS:180 platforms; a microparticle-based immunoassay (Abbott Laboratories, Abbott Park, Ill.) for BNP that is run on the AXSYM platform; and a chemiluminescent immuno-enzymatic assay (Biosite, Inc., San Diego, Calif.) for BNP that is run on the following Beckman Coulter platforms: Access, Access 2, Synchron LXI and the UniCel DXI. An electrochemiluminescent assay (Roche Diagnostics, Indianapolis, Ind.) available for measuring NT-proBNP.

The reference ranges for BNP and NTproBNP vary depending on a number of factors. The following ranges are for use where BNP levels are measured using an ELISA-type method, and one of skill in the art will be able to determine what levels obtained using other methods are equivalent. If the BNP level is >500 pg/mL, then HF is highly likely. Levels of BNP of 100-500 pg/mL are often described as a "grey zone," in which diagnosis is less certain. In lean subjects, if the BNP is <100 pg/mL, then HF is unlikely, however, obesity influences the expression of BNP in chronic HF (Mehra et al., J Am Coll Cardiol. 43(9):1590-1595 (2004)), so levels of <100 pg/mL do not rule out heart failure in obese subjects (Silver et al., Cong. Heart Fail. 10(5 suppl. 3):1-30 (2004)).

D-Dimers

A D-dimer is a stable end-product of fibrin degradation. Increased levels of D-dimers in the blood are associated with enhanced fibrin formation and fibrinolysis, and thus are diagnostic of conditions associated with these processes.

Methods for assaying D-dimer levels in the blood are known in the art. Commercially available assay kits include the VIDAS D-Dimer Exclusion (bioMérieux, Durham, N.C.) a rapid, automated ELISA; Minutex® D-dimer, Biopool Auto-Dimer™ (an automated, immunoturbidimetric assay for analysers reading at wavelengths of 540-880 nm), MiniQuant™, AMAX Auto D-Dimer™ (Automated D-dimer assay for AMAX instruments), and Accuclot D-Dimer™ assays (a semi-quantitative assay) (Trinity Biotech, Bray, Co. Wicklow, Ireland); and the HemosIL™ D-Dimer assay (Instrumentation Laboratory, distributed by Beckman Coulter), a fully automated immunoturbidimetric assay.

Plasma D-Dimer levels above 4000 µg/L are highly correlated with the presence of acute PE, and levels below 500 can be used to rule out PE (see, e.g., Perrier et al., Am. J. Respir. Crit. Care Med., 156(2):492-496 (1997)). Plasma D-dimer level of 500-4000 µg/L are more ambiguous, due to the number of conditions that activate the coagulation and fibrinolytic processes.

Other Biomarkers

The methods described herein can also include measuring levels of other biomarkers in addition to ST2 and/or IL-33. Suitable biomarkers include NT-proBNP, proBNP, BNP, NT-proANP, proANP, ANP, troponin, CRP, creatinine, D-dimers (degradation products of cross-linked fibrin, whose level becomes elevated following clot formation), BUN (blood-urea-nitrogen), liver function enzymes, albumin, IL-6 and/or bacterial endotoxin. Methods for measuring these biomarkers are known in the art, see, e.g., U.S. Pat. Pub. Nos. 2004/0048286 and 2005/0130136 to Lee et al.; Dhalla et al., Mol. Cell Biochem. 87:85-92 (1989); Moe et al., Am. Heart J. 139:587-95 (2000), the entire contents of which are incorporated herein by reference. Liver function enzymes include Alanine transaminase (ALT); Aspartate transaminase (AST) Alkaline phosphatase (ALP) and Total bilirubin (TBIL).

In these embodiments, levels of ST2 and one or more additional biomarkers are determined, and the information from the comparison of the biomarkers with their respective reference levels provides additional information regarding the presence of CVD in the subject, and/or the level of severity of CVD in the subject.

EXAMPLES

The invention is further described in the following examples, which do not limit the scope of the invention described in the claims.

Example 1: Sandwich ELISA Assay

This example uses the ST2 ELISA Kit manufactured by Medical & Biological Laboratories Co., Ltd. (MBL International Corp., Woburn, Mass.), no. 7638. This kit is a sandwich ELISA assay utilizing monoclonal antibodies for both capture and detection. This procedure is intended to analyze a full plate of samples assayed in replicates at a 1:3 dilution factor and closely follows the manufacturers' protocol. Kits should be stored at 4° C. until use. The procedure described in this example is optimized for human serum or plasma collected in citrate or EDTA anticoagulant tubes. Plasma collected in heparin anticoagulant tubes should not be used in this assay as heparin binds ST2 and inhibits measurement by this ELISA protocol. Plasma or serum samples may be used fresh or stored frozen. This assay is not adversely affected by up to 3 freeze and thaw cycles of plasma samples.

Reagents should be prepared fresh from a new kit immediately before performing the assays. Allow the kit to equilibrate to room temperature prior to use. Reagents not explicitly discussed below are provided by the manufacturer ready to use.
1. Wash solution—wash solution is provided by the manufacturer as a 10X concentrate solution. To make 1 liter of wash solution dilute 100 ml of the 10X concentrate provided with 900 ml of distilled water.
2. Detector solution—the detector solution is prepared by diluting the detector concentrate 1:101 with the detector diluent. For a full 96 well plate of samples 10 ml of detector solution is required. To prepare 10 ml of detector solution use a pipette to transfer 10 ml of the blue colored detector diluent to a 15 ml orange top polypropylene tube. Ad 100 µl of the detector concentrate to this volume of detector diluent.
   a. NOTE: this reagent should be prepared during the first assay incubation step.
3. Calibrator stock—reconstitute the calibrator protein by dissolving the lyophilized protein in the amount of distilled water defined by the manufacturer for this manufacturing lot to yield a stock solution of 8 ng/ml. This volume specification is included in the product insert.

Preparation of standards and samples:

All of the following should be prepared in labeled 1.5 ml polypropylene tubes to be transferred to the assay plate with the P200 pipetter.

Standards:

The standard curve is prepared by making 2 fold serial dilutions of the 8 ng/ml stock solution.
1. Using a P1000 pipette transfer 250 µl of Assay Diluent to 8 1.5 ml polypropylene tubes labeled S1-S8
2. Using the same P1000 pipette transfer 250 µl of the 8 ng/ml Calibrator stock solution to tube S1. This tube is now 4 ng/ml calibrator protein.
   a. Mix thoroughly by gently pipetting 3 times being careful not to create bubbles.
3. Using the same P1000 pipette and a fresh tip for each of the following transfer 250 µl of the reagent in tube S1 to tube S2, repeat the mixing.
4. Repeat step 3 for S2 to S3, S3 to S4, S4 to S5, S5 to S6 and S6 to S7. S8 will be the reagent blank so do not transfer the calibrant protein to this well.
   a. Tubes S1-S6 and S8 will now have 250 µl of reagent and tube S7 will have 450 µl.

Samples:

The plate is set up so that each sample is analyzed as a 1:3 dilution in duplicate. An exemplary set up is shown below in Table 4.
1. Label a 1.5 ml polypropylene tube for each sample.
2. Using the P200 pipette transfer 160 µl of Assay Diluent to each tube.
3. Using a P200 pipette transfer 80 µl of serum or plasma from sample 1 to tube
   1. Mix carefully by pipetting 3 times without making bubbles.
4. Continue transferring samples to the sample tubes by repeating step 2 for each sample.

Procedure:
1. Use the P200 pipette transfer the standards and diluted serum samples quickly to the 96 well assay plate.
   a. Set the P200 pipette for 100 µl
   b. Transfer 100 µl of the standard curve dilutions to each of columns 1 & 2 in the assay plate
   c. Transfer 100 µl of each of the serum samples to the assay plate in exactly the same positions as shown in the plate map below.
2. Cover the assay plate with the provided shield and incubate at room temperature for 60 minutes.
3. Using the plate autowasher wash the plate 4 times.
4. Detector: using the 8 channel multichannel pipette transfer 100 µl of the detector solution to each well and incubate at room temperature for 60 minutes.
   a. NOTE: this reagent was to be prepared during the first incubation step.
   b. NOTE: use a disposable reagent vessel for this reagent addition. ALWAYS use a fresh disposable reagent vessel for each reagent. It is not necessary to change pipette tips during this step.
5. Wash the plate as in step 3
6. Substrate: using the 8 channel multichannel pipette transfer 100 µl of the Substrate to each well and incubate at room temperature for 30 minutes.
   a. The Substrate reagent is provided ready to use by the manufacturer.
7. Stop: at the completion of the Substrate incubation using the 8 channel multichannel pipette transfer 100 µl of the Stop solution to each well.
   a. The Stop Solution reagent is provided ready to use by the manufacturer.
8. Read the plate at 450 nm with background correction at 620 nm.
   a. The plate should be read within 30 minutes after stopping the reaction.
9. Enter the absorbance readings in the provided spreadsheet for analysis.

TABLE 4

| Map of Exemplary 96 Well Assay Plate | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 4.0 | | 1 | 1 | 9 | 9 | 17 | 17 | 25 | 25 | 33 | 33 |
| B | 2.0 | | 2 | 2 | 10 | 10 | 18 | 18 | 26 | 26 | 34 | 34 |
| C | 1.0 | | 3 | 3 | 11 | 11 | 19 | 19 | 27 | 27 | 35 | 35 |
| D | 0.5 | | 4 | 4 | 12 | 12 | 20 | 20 | 28 | 28 | 36 | 36 |

TABLE 4-continued

Map of Exemplary 96 Well Assay Plate

|   | 1 | 2 | 3 | 4 | 5 | 6 | 7 | 8 | 9 | 10 | 11 | 12 |
|---|---|---|---|---|---|---|---|---|---|----|----|----|
| E | 0.25 |  |  | 5 | 5 | 13 | 13 | 21 | 21 | 29 | 29 | 37 | 37 |
| F | 0.125 |  |  | 6 | 6 | 14 | 14 | 22 | 22 | 30 | 30 | 38 | 38 |
| G | 0.0625 |  |  | 7 | 7 | 15 | 15 | 23 | 23 | 31 | 31 | 39 | 39 |
| H | 0.0 |  |  | 8 | 8 | 16 | 16 | 24 | 24 | 32 | 32 | 40 | 40 |

Example 2: PRAISE-2

The Second Prospective Randomized Amlodipine Survival Evaluation (PRAISE-2) study was a double-blind, randomized trial prospectively designed to identify echocardiographic predictors of survival among patients with non-ischemic cardiomyopathy and heart failure and to determine if components of the echocardiographic examination add prognostic information to baseline demographic and clinical information (Cabell et al., Am. Heart J. 147(1):151-7 (2004)). One hundred patients participated in the PRAISE-2 echocardiographic study; of these, 93 had full and interpretable echocardiographic examinations. Serum samples were drawn at baseline and 2 weeks, and IL1LR1 levels were determined as described in Example 1.

Receiver operating characteristic (ROC) curve analysis using Analyse-It software (Analyse-It, Ltd, Leeds, UK). The ROC curve is shown in FIG. 1, and AUC (area under the curve) information for the same parameters shown in FIG. 1 is given below in Table 5. The ROC analysis provides a summary of all of the markers that were evaluated for prognostic value at baseline (t1). An AUC would indicate a neutral result; any result above 0.5 indicates an increase in accuracy of prediction based on that measurement, whereas a result below 0.5 indicates a loss of accuracy (i.e., the variability is high for that marker), and no correlation with the measured parameter.

TABLE 5

PRAISE ROC Results

| Variable | AUC | p |
|---|---|---|
| Age | 0.620 | 0.027 |
| Height | 0.562 | 0.250 |
| Weight | 0.425 | 0.168 |
| BMI | 0.391 | 0.043 |
| LVEF | 0.421 | 0.146 |
| Creatinine | 0.599 | 0.066 |
| ST2t1 | 0.611 | 0.040 |
| NEt1 | 0.632 | 0.015 |
| Et1 | 0.496 | 0.941 |
| DAt1 | 0.637 | 0.012 |
| ANGt1 | 0.471 | 0.587 |
| MDAt1 | 0.541 | 0.451 |
| ADRt1 | 0.504 | 0.934 |
| ANPt1 | 0.811 | 0.000 |
| BNPt1 | 0.779 | 0.000 |

The value of ST2 for endpoint prediction was compared to other markers in three BMI groups. The results, shown in Table 6, below, indicate that for patients with a high BMI, ST2 (e.g., the ratio of ST2) is a stronger predictor than BNP. The negative numbers in the middle weight group for ST2 may be due to the presence of anomalous levels in some subjects.

TABLE 6

PRAISE Endpoint Prediction in 3 BMI Groups

| BMI Group | Predictor | R | S.E. | Sig. |
|---|---|---|---|---|
| Under 25 | Log BNP time 0 | 2.472 | 1.301 | 0.058 |
|  | Age | 0.032 | 0.032 | 0.319 |
|  | Sex | 0.274 | 0.986 | 0.781 |
|  | ST2 Ratio | 3.094 | 1.997 | 0.121 |
| 25 to 30 | Log BNP time 0 | 4.031 | 1.467 | 0.006 |
|  | Age | 0.042 | 0.037 | 0.258 |
|  | Sex | −0.516 | 0.960 | 0.591 |
|  | ST2 Ratio | −0.764 | 1.643 | 0.642 |
| 30 and over | Log BNP time 0 | 1.283 | 0.966 | 0.184 |
|  | Age | 0.008 | 0.039 | 0.844 |
|  | Sex | −2.128 | 1.056 | 0.044 |
|  | ST2 Ratio | 6.581 | 2.539 | 0.010 |

Figure 2:
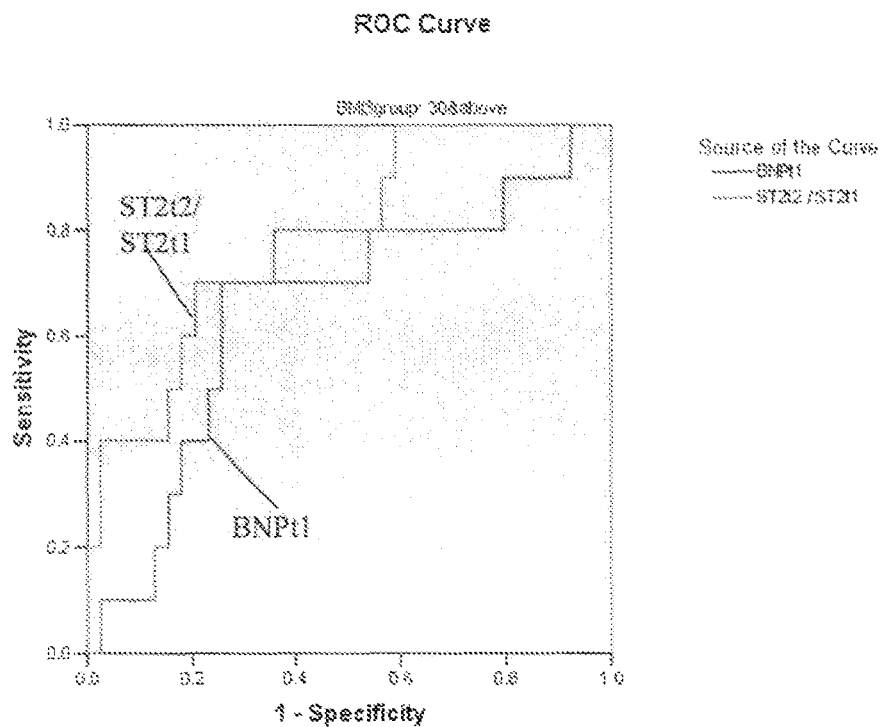
FIG. 2 is a ROC curve for BNP and ST2 Ratio in the PRAISE-2 study; the two measures have similar AUC, with BNP somewhat higher.

The PRAISE ROC for BNP and ST2 Ratio was also calculated. The results, shown in FIG. 2 and Table 7, indicate that ST2 ratio is comparable to BNP across the entire PRAISE population, which included both non-overweight, non-obese subjects, as well as subjects in whom HF was stabilized; ST2 levels tend to return to baseline when HF is stabilized.

TABLE 7

ROC for BNP and ST2 Ratio

| Predictor | AUC | SE | P | Lower | Upper |
|---|---|---|---|---|---|
| BNPt1 | 0.783 | 0.043 | 0.000 | 0.698 | 0.868 |
| ST2-Ratio | 0.660 | 0.054 | 0.004 | 0.555 | 0.766 |

Figure 3:
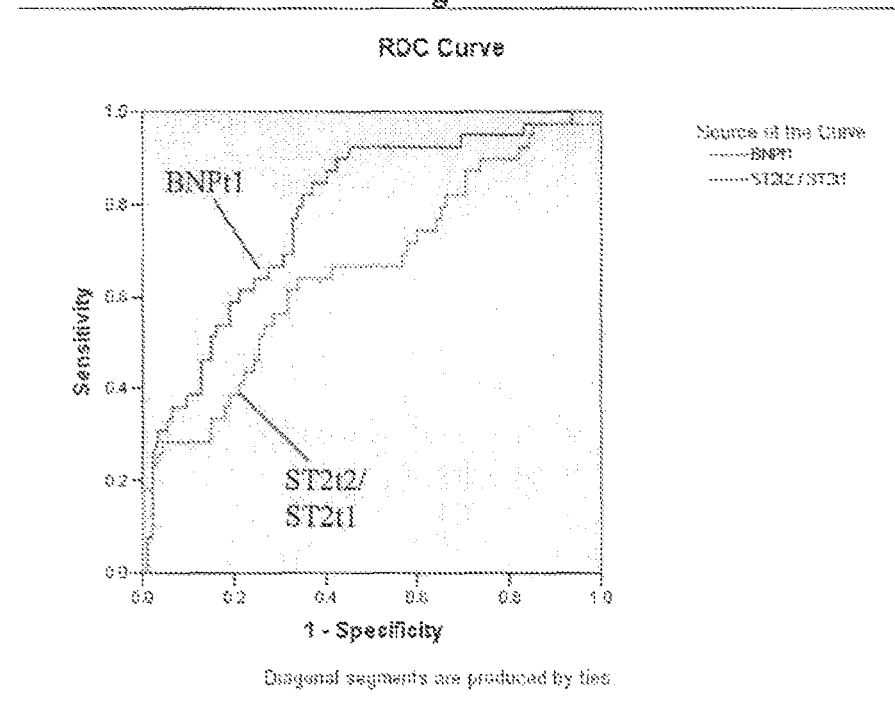
FIG. 3 is a ROC curve for prognostic utility of BNP and ST2 ratio in high BMI individuals; in this case, ST2 ratio has a greater AUC.

Prognostic utility of BNP and ST2 Ratio was calculated for those individuals with high BMI; the results, shown in Table 8 and FIG. 3, demonstrate that ST2 ratio is a better predictor than BNP in the high BMI group, as it has a higher AUC and a better correlation.

TABLE 8

Prognostic Utility for BNP and ST2 Ratio in High BMI

| BMI Group | Predictor | AUC | SE | P | Lower | Upper |
|---|---|---|---|---|---|---|
| Under 25 | BNP Baseline | 0.788 | 0.077 | 0.002 | 0.637 | 0.939 |
|  | ST2 Ratio | 0.717 | 0.082 | 0.022 | 0.555 | 0.878 |
| 25-29 | BNP Baseline | 0.864 | 0.055 | 0.000 | 0.756 | 0.972 |
|  | ST2 Ratio | 0.521 | 0.097 | 0.829 | 0.330 | 0.711 |
| 30 and Above | BNP Baseline | 0.669 | 0.100 | 0.102 | 0.473 | 0.865 |
|  | ST2 Ratio | 0.772 | 0.083 | 0.009 | 0.609 | 0.934 |

These results indicate that ST2 is predictive of outcome in the compensated heart failure patient when used as a change over time, and provides additional prognostic resolution in high BMI patients.

Example 2: ST2 Is Not Affected by BMI 600 breathless subjects were enrolled in the PRIDE study to analyze the utility of NT-proBNP for diagnosis and prognosis of acute heart failure (HF). At enrollment, a blinded sample of blood was obtained, processed and frozen at −80° C. For the purposes of ST2 analysis, an aliquot of citrated blood was thawed (second freeze-thaw cycle) and analyzed for concentration of ST2 protein. The effect of BMI on ST2 levels was analyzed.

The results are shown in FIG. 4 and Table 9. ST2 median values were the same across all three BMI groups, and the IQR was nearly identical as well.

TABLE 9

BMI and ST2 levels

| BMI | ST2 (median, ng/ml) | Interquartile range (ng/ml) |
|---|---|---|
| <25 (n = 77) | 0.56 | 0.31-1.39 |
| 25-29.9 (n = 65) | 0.49 | 0.23-1.13 |
| ≥30 (n = 66) | 0.48 | 0.23-1.04 |

These results demonstrate that, unlike BNP, ST2 levels are not affected by BMI.

Example 3. ST2 Concentrations are Not Affected by Renal Insufficiency

The effect of renal impairment on ST2 concentrations was evaluated in a population of 135 patients with moderate to severe renal insufficiency. None of the patients were on dialysis, and none were previously diagnosed with CVD. All of the patients were evaluated using glomerular filtration rate (GFR in mls/min) as determined by the Modification of Diet in Renal Disease (MDRD) method as a measure of renal function. Echocardiography and coronary artery calcium (CAC) measurements were also performed on each subject to detect latent CVD. Multiple biomarkers were also evaluated.

The descriptive statistics for this cohort are shown in Table 10; the mean GFR and ST2 are illustrated graphically in FIGS. 5A-B.

TABLE 10

Glomerular Filtration Rate (GFR) and ST2 Levels

|  | GFR | ST2 levels (ng/ml) |
|---|---|---|
| Mean | 34.5 | 0.122 |
| Median | 34 | 0.107 |
| Std Error | 0.989 | 0.005 |
| Std Dev. | 11.4 | 0.059 |
| Coeff. Var. | 33.3 | 48.346 |
| Lower 95% CL | 32.5 | 0.112 |
| Upper 95% CL | 36.4 | 0.132 |
| 25th Percentile | 27 | 0.090 |
| 75th Percentile | 43 | 0.127 |
| Minimum | 9 | 0.068 |
| Maximum | 59 | 0.476 |
| Count | 135 | 135 |

Figure 6:
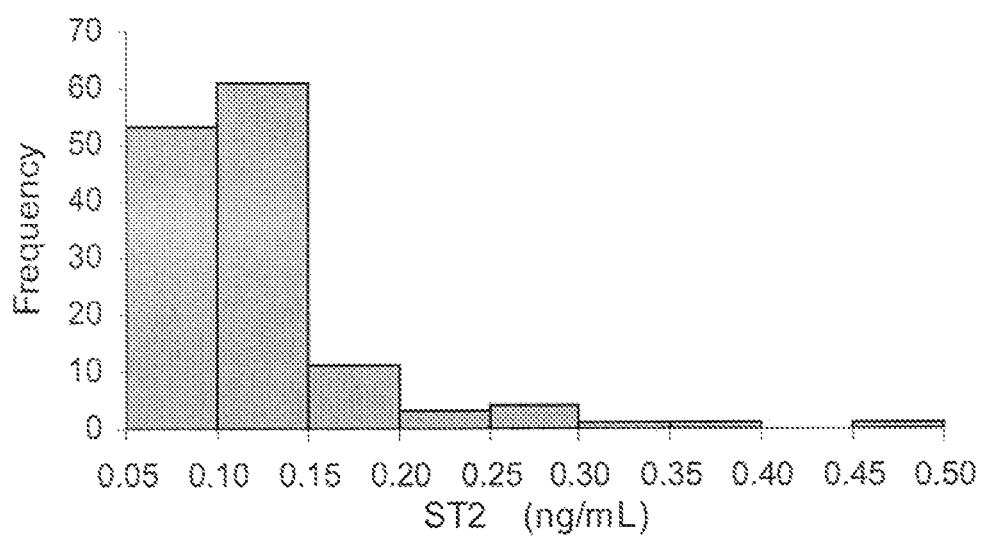
FIG. 6 is a bar graph illustrating the distribution of ST2 levels in the population described in Example 3, showing that the vast majority of subjects in the population have levels of ST2 that are below 0.2 ng/ml.

In this cohort of patients with stable, chronic disease, only ten (8%) had ST2 levels above 0.2, the highest of which was 0.476 ng/ml. This distribution of ST2 values is shown in FIG. 6. This was as expected in this population of subjects with chronic, managed renal insufficiency; one would not expect to see very high ST2 levels.

Pearson Correlation analysis was performed in this population to determine whether there was a correlation between ST2 levels and renal function, as measured by either GFR or creatinine clearance. The results are shown in Tables 11 and 12.

TABLE 11

Pearson Correlation Results - GFR and ST2

Descriptive Statistics

| Variable | Mean | Std Dev. | Std Err | N |
|---|---|---|---|---|
| GFR | 34.5 | 11.5 | 0.989 | 135 |
| ST2 (ng/mL) | 0.122 | 0.059 | 0.005 | 135 |

|  | GFR | ST2 (ng/mL) |
|---|---|---|
| Correlation Matrix (R) | | |
| GFR | 1.000 | 0.028 |
| ST2 (ng/mL) | 0.028 | 1.000 |
| Correlation Significance (P) | | |
| GFR | — | 0.748 |
| ST2 (ng/mL) | 0.748 | — |

TABLE 12

Pearson Correlation Results - Creatinine Clearance and ST2

Descriptive Statistics

| Variable | Mean | Std Dev. | Std Err | N |
|---|---|---|---|---|
| Screening Cr | 2.175 | 0.859 | 0.081 | 113 |
| ST2 (ng/mL) | 0.122 | 0.058 | 0.006 | 113 |

|  | Screening Cr | ST2 (ng/mL) |
|---|---|---|
| Correlation Matrix (R) | | |
| Screening Cr | 1.000 | −0.018 |
| ST2 (ng/mL) | −0.018 | 1.000 |
| Correlation Significance (P) | | |
| Screening Cr | — | 0.851 |
| ST2 (ng/mL) | 0.851 | — |

These results demonstrate that, as was expected in this population of subjects with chronic, managed renal insufficiency, there is no correlation between ST2 levels and either GFR (p=0.75) or creatinine clearance (p=0.851) in this population. This indicates that renal insufficiency, by itself, does not cause an elevation of ST2 levels.

The same analyses were carried out in a population of 139 subjects at the San Diego Veteran's Administration Hospital. All of the subjects had previously been diagnosed with acute decompensated heart failure (ADHF), and the mean ST2 level was about twice that seen in the population of patients with chronic renal insufficiency but no HF (see Tables 11-12). There is an almost ubiquitous correlation between renal insufficiency and heart failure, with an almost 80% confluence of patients with stage III/IV HF also having impaired renal function (Fonarow and Heywood, Am. J. Med. (2006) 119(12A):S17-S25. Thus, because ADHF is correlated with ST2 levels, one would expect to see a correlation between renal insufficiency (as measured by GFR) and ST2 levels. This was exactly what was seen, as shown in Tables 13 and 14.

TABLE 13

Pearson Correlation Results - GFR and ST2 in ADHF

Descriptive Statistics

| Variable | Mean | Std Dev. | Std Err | N |
|---|---|---|---|---|
| GFR | 59.1 | 25.3 | 2.143 | 139 |
| ST2 (ng/mL) | 0.283 | 0.332 | 0.028 | 139 |

| | GFR | ST2 (ng/mL) |
|---|---|---|
| Correlation Matrix (R) | | |
| GFR | 1.000 | −0.062 |
| ST2 (ng/mL) | −0.062 | 1.000 |
| Correlation Significance (P) | | |
| GFR | — | 0.470 |
| ST2 (ng/mL) | 0.470 | — |

TABLE 14

Pearson Correlation Results - GFR and ST2 Ratios in ADHF

Descriptive Statistics

| Variable | Mean | Std Dev. | Std Err | N |
|---|---|---|---|---|
| GFR | 59.1 | 25.3 | 2.143 | 139 |
| ST2 ratio | 1.038 | 3.038 | 0.258 | 139 |

| | GFR | ST2 ratio |
|---|---|---|
| Correlation Matrix (R) | | |
| GFR | 1.000 | −0.161 |
| ST2 ratio | −0.161 | 1.000 |
| Correlation Significance (P) | | |
| GFR | — | 0.058 |
| ST2 ratio | 0.058 | — |

These results demonstrate that, in subjects with ADHF, ST2 values, whether represented as a single level or a ratio, are correlated with measures of renal insufficiency, but are independent of the renal insufficiency; thus, there is no causative relationship between the two. Rather, both variables are related to and independently interact with a third parameter (in this case, heart failure).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing heart failure in a subject who has one or both of a body mass index (BMI) of greater than or equal to 25, and impaired renal function, and treating the subject, the method comprising:
   (a) one or both of:
      (i) determining the subject's BMI, and if the subject's BMI is equal to or greater than 25, selecting the subject; and
      (ii) evaluating the subject's renal function, and if the subject has impaired renal function, selecting the subject;
   (b) performing an immunoassay to determine a level of brain natriuretic peptide (BNP) and a level of soluble ST2 in a biological sample from the selected subject;
   (c) identifying a selected subject having a BNP level of between 100 pg/mL and 500 pg/mL, and an elevated level of soluble ST2 as compared to a reference level of soluble ST2 as having heart failure; and
   (d) administering a pharmaceutical treatment for heart failure to the identified subject.

2. The method of claim 1, wherein the biological sample comprises blood, plasma, or serum.

3. The method of claim 1, wherein the reference level of soluble ST2 represents a level of soluble ST2 in a subject who does not have heart failure.

4. The method of claim 2, wherein the reference level of soluble ST2 is about 0.2 ng/mL of serum, and values above that level indicate, in part, the presence of heart failure.

5. The method of claim 1, further comprising performing an assay to determine a level of one or more other biomarkers in the subject.

6. The method of claim 5, wherein the one or more other biomarkers are selected from the group consisting of atrial natriuretic peptide (ANP), N-terminal-proANP, troponin, C-reactive protein, creatinine, Blood Urea Nitrogen, liver function enzymes, and albumin.

7. The method of claim 1, wherein determining whether the subject has impaired renal function comprises determining glomerular filtration rate (GFR) and/or serum creatinine level, and determining that the subject has impaired renal function if they have a GFR or serum creatinine level as shown in the following table:

| Grade | GFR (ml/minute) | Serum Creatinine (µmol/liter) |
|---|---|---|
| mild | 20-50 | 150-300 |
| moderate | 10-20 | 300-700 |
| severe | <10 | >700. |

8. The method of claim 1, wherein the subject has a BMI of greater than or equal to 30.

9. The method of claim 1, wherein the subject has a BMI of 25 to 29.

10. The method of claim 1, wherein the immunoassay is an enzyme-linked immunosorbent assay (ELISA).

11. A method of diagnosing heart failure in a subject who has impaired renal function, and treating the subject, the method comprising:
   (a) evaluating the subject's renal function, and if the subject has impaired renal function, selecting the subject;
   (b) performing an immunoassay to determine a level of soluble ST2 in a biological sample from the selected subject;
   (c) identifying a selected subject having an elevated level of soluble ST2 as compared to a reference level of soluble ST2 as having heart failure; and
   (d) administering to the identified subject a pharmaceutical treatment for heart failure.

12. The method of claim 11, wherein the reference level of soluble ST2 represents a level in a subject who does not have heart failure.

13. The method of claim 11, wherein the reference level of soluble ST2 is about 0.2 ng/mL of serum, and values above that level indicate that the subject has heart failure.

14. The method of claim 11, wherein the biological sample comprises blood, plasma, or serum.

15. The method of claim 11, further comprising performing an assay to determine a level of one or more other biomarkers in the subject.

16. The method of claim 15, wherein the one or more other biomarkers are selected from the group consisting of: brain natriuretic peptide, D-Dimer, atrial natriuretic peptide (ANP), N-terminal-proANP, troponin, C-reactive protein, creatinine, Blood Urea Nitrogen, liver function enzymes, and albumin.

17. The method of claim 11, wherein determining whether the subject has impaired renal function comprises determining glomerular filtration rate (GFR) and/or serum creatinine level, and determining that the subject has impaired renal function if they have a GFR or serum creatinine level as shown in the following table:

| Grade | GFR (ml/minute) | Serum Creatinine (µmol/liter) |
| --- | --- | --- |
| mild | 20-50 | 150-300 |
| moderate | 10-20 | 300-700 |
| severe | <10 | >700. |

18. The method of claim 11, wherein the immunoassay is an enzyme-linked immunosorbent assay (ELISA).

* * * * *